United States Patent
Ziv et al.

(10) Patent No.: US 11,123,172 B2
(45) Date of Patent: Sep. 21, 2021

(54) DEVICES AND METHODS FOR THE AMELIORATION OF FECAL INCONTINENCE

(71) Applicant: ConTIPI Medical Ltd., Caesarea (IL)

(72) Inventors: Elan Ziv, Ramat-Gan (IL); Zohar Tyroler, Hod-HaSharon (IL); Tal Caspi, Pardes Chana-Karkur (IL)

(73) Assignee: ConTIPI Medical Ltd., Caesarea (IL)

( * ) Notice: Subject to any disclaimer, the term of this patent is extended or adjusted under 35 U.S.C. 154(b) by 232 days.

(21) Appl. No.: 16/344,809

(22) PCT Filed: Oct. 30, 2017

(86) PCT No.: PCT/IL2017/051182
§ 371 (c)(1),
(2) Date: Apr. 25, 2019

(87) PCT Pub. No.: WO2018/078635
PCT Pub. Date: May 3, 2018

(65) Prior Publication Data
US 2020/0054427 A1 Feb. 20, 2020

Related U.S. Application Data

(60) Provisional application No. 62/414,743, filed on Oct. 30, 2016.

(51) Int. Cl.
*A61F 2/00* (2006.01)

(52) U.S. Cl.
CPC ............ *A61F 2/005* (2013.01); *A61F 2/0009* (2013.01)

(58) Field of Classification Search
CPC .............................. A61F 2/0009; A61F 2/005
See application file for complete search history.

(56) References Cited

U.S. PATENT DOCUMENTS

| 5,782,745 A | 7/1998 | Benderev |
| 2007/0203429 A1 | 8/2007 | Ziv |
| 2013/0053863 A1 | 2/2013 | Juravic et al. |

FOREIGN PATENT DOCUMENTS

| CN | 104689459 | 6/2015 |
| RU | 2358691 | 6/2009 |
| WO | WO 2005/065575 | 7/2005 |
| WO | WO 2011/121591 | 10/2011 |
| WO | WO 2018/078635 | 5/2018 |

OTHER PUBLICATIONS

International Preliminary Report on Patentability dated May 9, 2019 From the International Bureau of WIPO Re. Application No. PCT/IL2017/051182. (10 Pages).

(Continued)

*Primary Examiner* — Christine H Matthews

(57) ABSTRACT

A fecal incontinence device for insertion into a vagina, comprising: a plurality of shell segments, which together form an enclosed cylinder with rounded ends in a collapsed state of the device, wherein one of the cylindrical shells is disposed in the device facing a posterior wall of the vagina when the device is inserted into the vagina; a pressure generating structure attached to and abutting the posterior-facing cylindrical shell; and, a state-changing mechanism configured to reversibly transition the device from the collapsed state to an expanded state.

20 Claims, 29 Drawing Sheets

(56) References Cited

OTHER PUBLICATIONS

International Search Report and the Written Opinion dated Apr. 30, 2018 From the International Searching Authority Re. Application No. PCT/IL2017/051182. (17 Pages).

Invitation to Pay Additional Fees dated Mar. 5, 2018 From the International Searching Authority Re. Application No. PCT/IL2017/051182. (2 Pages).

Supplementary European Search Report and the European Search Opinion dated May 4, 2020 From the European Patent Office Re. Application No. 17864097.5. (6 Pages).

Request for Examination and Search Report dated Feb. 4, 2021 From the Federal Government Institution, Federal Institute of Industrial Property of the Federal Service of Intellectual Property, Patents and Trademarks of the Russian Federation, FIPS Re. Application No. 2019115455 and Its Summary in English. (8 Pages)

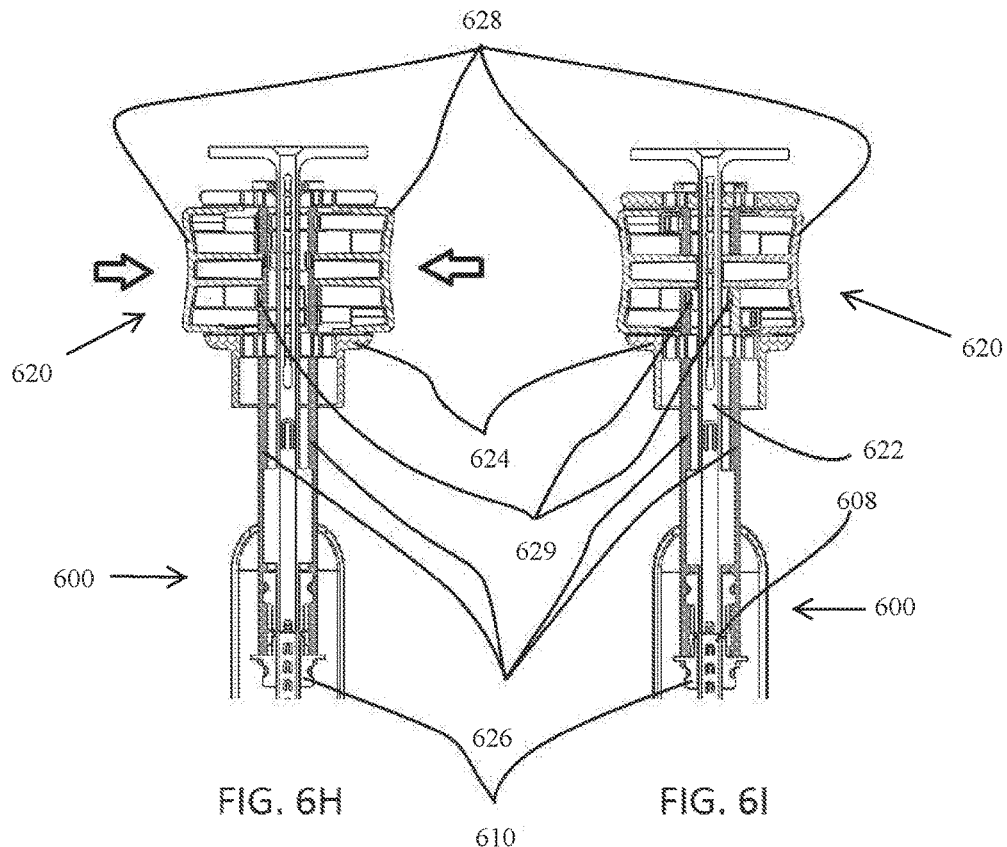
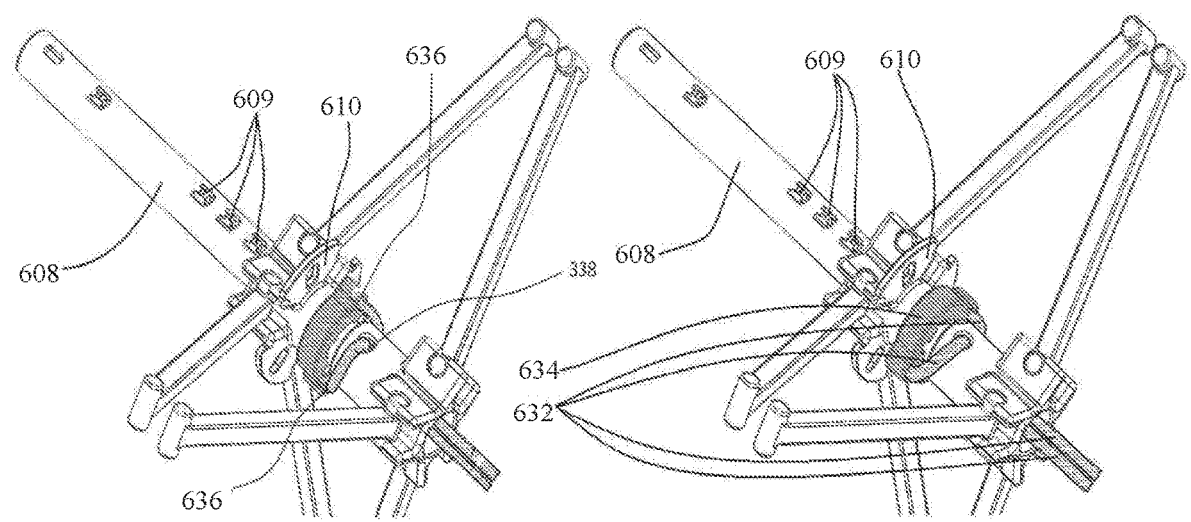
FIG. 6H   FIG. 6I
FIG. 6J   FIG. 6K

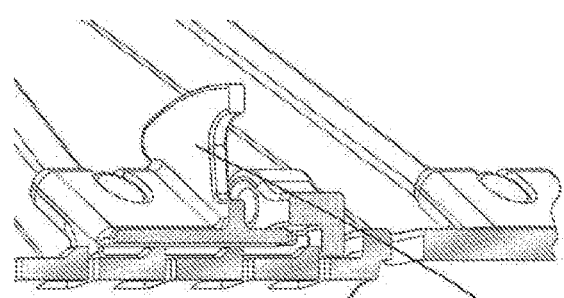
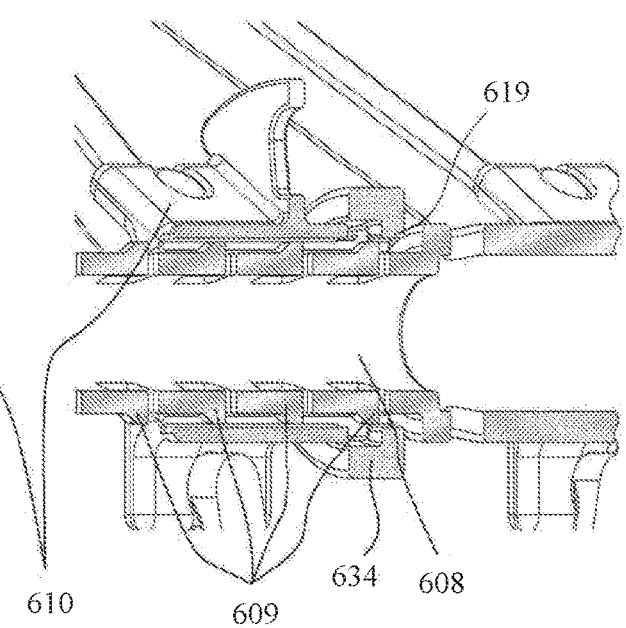
FIG. 6L
FIG. 6M
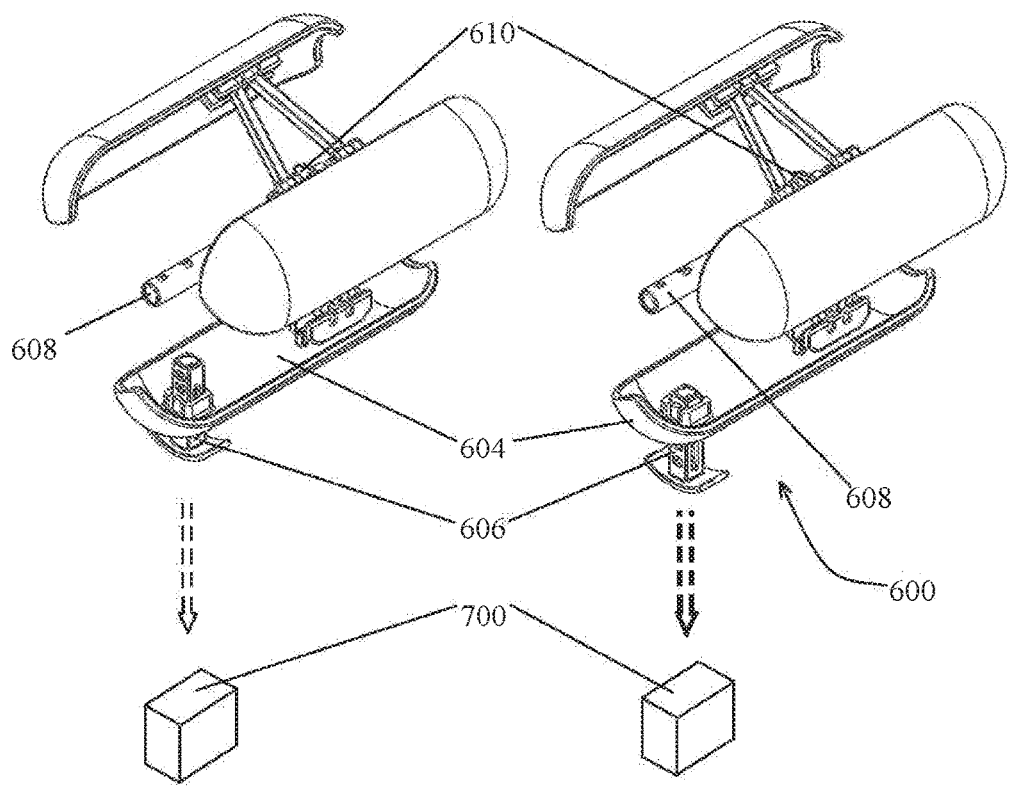
FIG. 7A
FIG. 7B

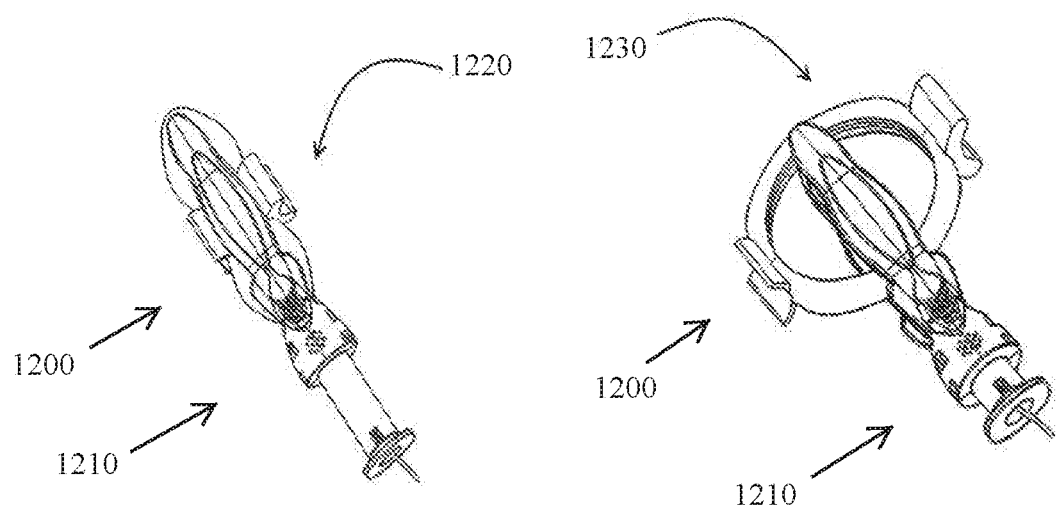
FIG. 12A
FIG. 12B
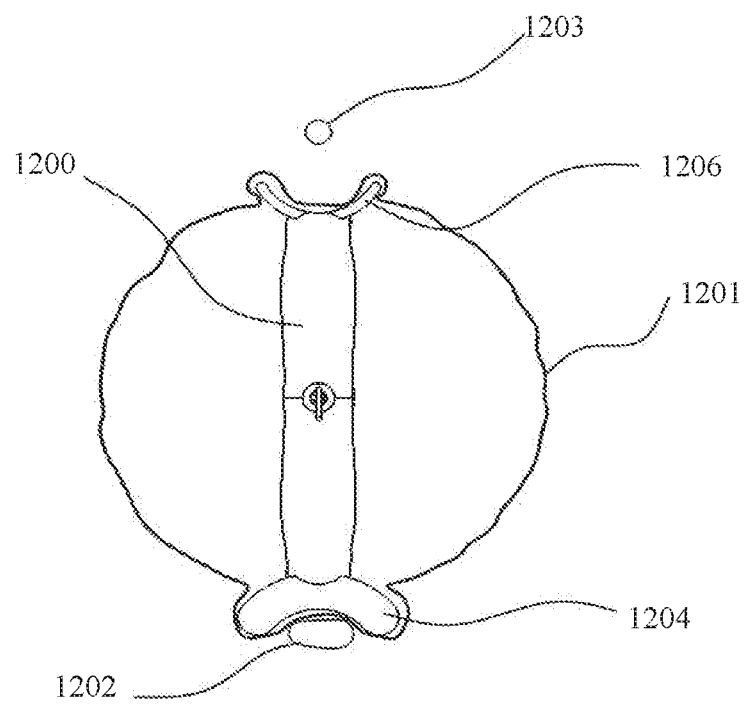
FIG. 12C

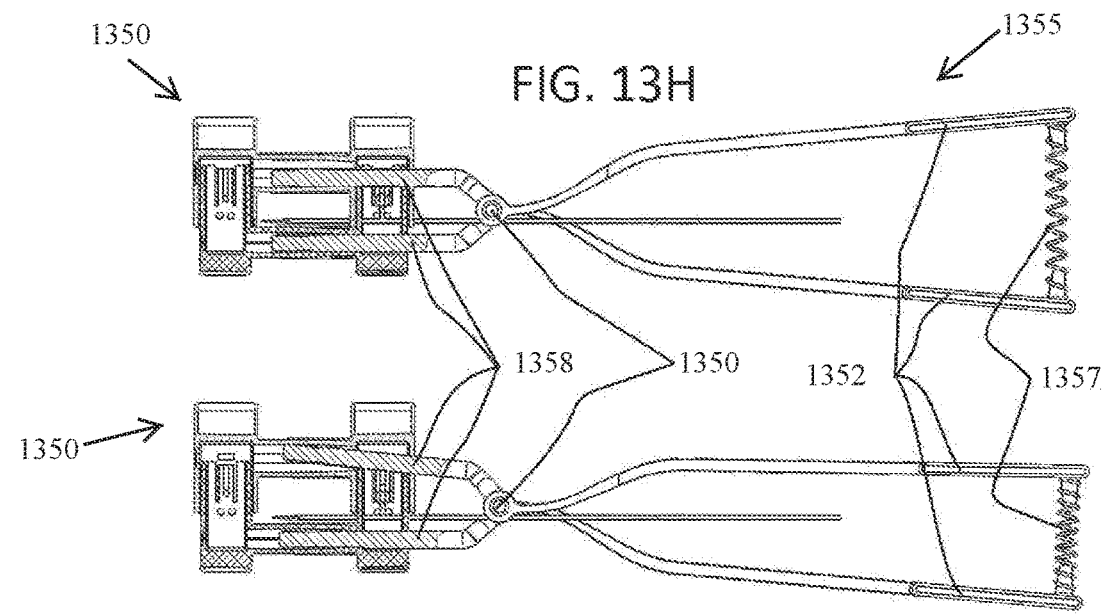
FIG. 13H
FIG. 13I
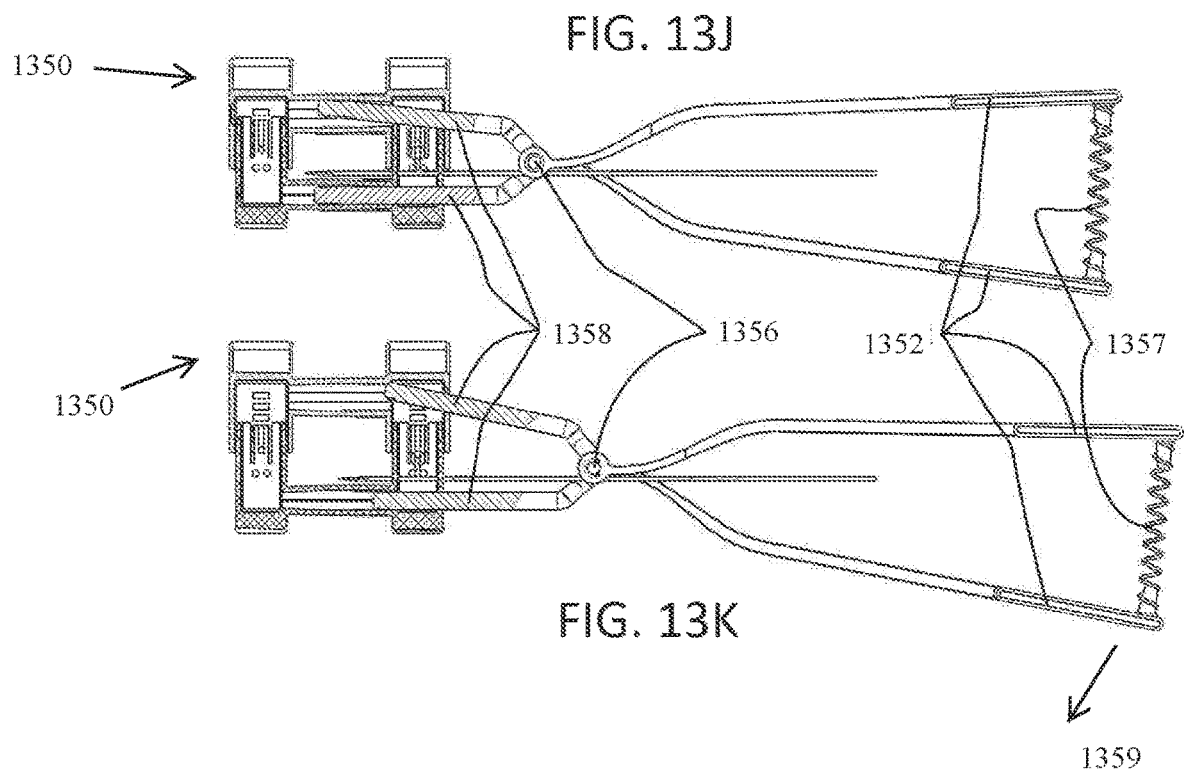
FIG. 13J
FIG. 13K

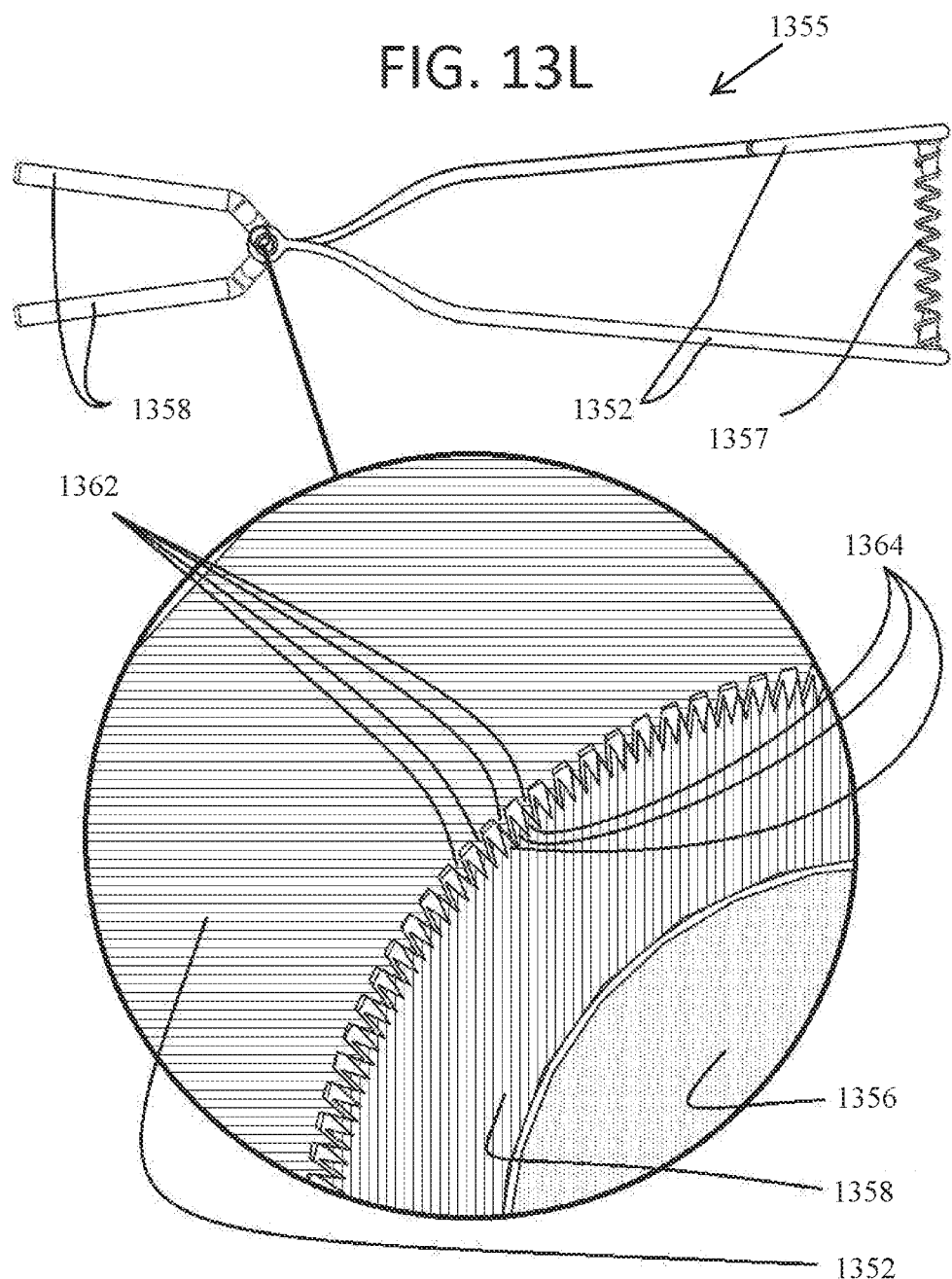

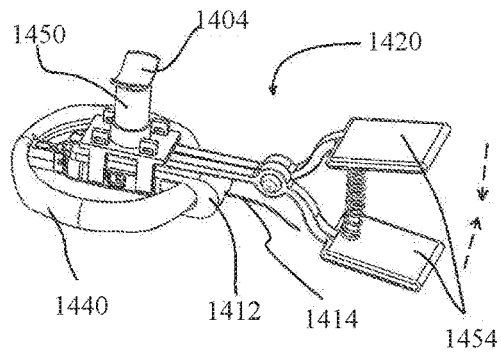
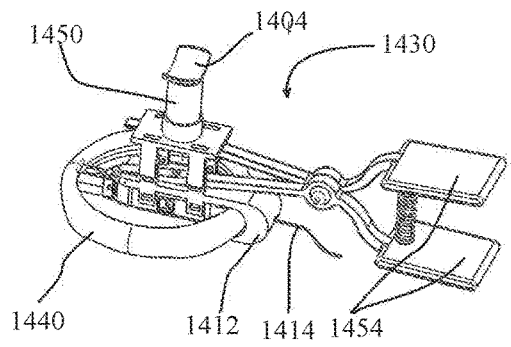
FIG. 14E  FIG. 14F
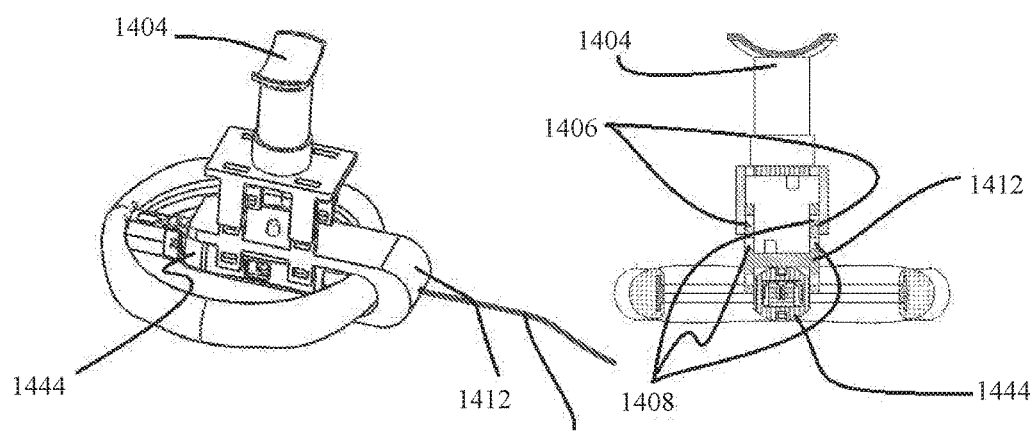
FIG. 14G  FIG. 14H
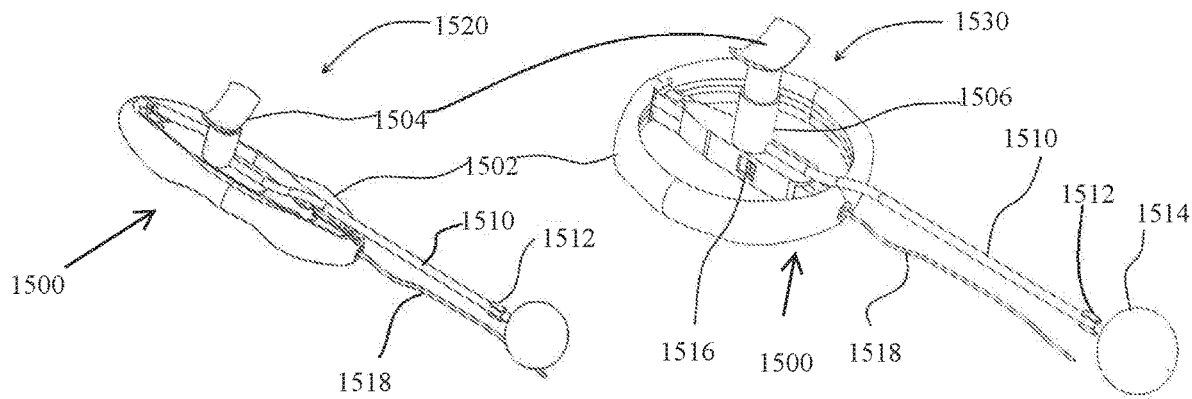
FIG. 15A  FIG. 15B

DEVICES AND METHODS FOR THE AMELIORATION OF FECAL INCONTINENCE

RELATED APPLICATIONS

This application is a National Phase of PCT Patent Application No. PCT/IL2017/051182 having International filing date of Oct. 30, 2017, which claims the benefit of priority under Article (8) PCT of U.S. Provisional Patent Application No. 62/414,743 filed on Oct. 30, 2016. The contents of the above applications are all incorporated by reference as if fully set forth herein in their entirety.

FIELD AND BACKGROUND OF THE INVENTION

The present invention, in some embodiments thereof, relates to health care and, more particularly, but not exclusively, to devices and methods for ameliorating fecal incontinence in women.

Fecal incontinence, also called a bowel control problem, is the accidental passing of solid or liquid stool or mucus from the rectum. Fecal incontinence includes the inability to hold a bowel movement until reaching a toilet as well as passing stool into one's underwear without being aware of it happening. Fecal incontinence has many causes, including: diarrhea, constipation, muscle damage or weakness, nerve damage, loss of stretch in the rectum, childbirth by vaginal delivery, hemorrhoids and rectal prolapse, rectocele (protrusion of the rectum through the vagina), and inactivity.

Previous attempts at treating fecal incontinence include: medications, dietary changes, exercise (biofeedback, bowel training, sacral nerve stimulation, posterior tibial nerve stimulation), vaginal balloons, and surgery (sphincteroplasty, sphincter replacement, sphincter repair, colostomy, surgical repair of rectal prolapse or rectocele or hemorrhoids).

Vaginal balloons are currently the only substitutional treatment to surgical procedures. However, vaginal balloons have several deficiencies, such as the need for inflation tube, lack of effective stable support, etc.

Background art includes the following patents, the contents of all of which are incorporated by reference as if fully set forth herein:

| | |
|---|---|
| WO 2011/116108 | Intra-Vaginal Device for Fecal Incontinence; |
| US 2014/0275746 | Intra-Vaginal Devices and Methods for treating Fecal Incontinence; |
| WO2008/102341 | Fecal incontinence device, kit and method; and, |
| US 2012/0277522 | Fecal incontinence device, system and method. |

SUMMARY OF THE INVENTION

There is provided in aspect of the invention, a fecal incontinence device for insertion into a vagina, comprising: a plurality of shell segments, which together form an enclosed cylinder with rounded ends in a collapsed state of the device, wherein one of the cylindrical shells is disposed in the device facing a posterior wall of the vagina when the device is inserted into the vagina; a pressure generating structure attached to and abutting the posterior-facing cylindrical shell, and, a state-changing mechanism configured to reversibly transition the device from the collapsed state to an expanded state.

In an embodiment of the invention, the device further comprises an applicator, removable from the device, inserted into the enclosed cylinder and configured to activate the state-changing mechanism to transition the device from the collapsed state to the expanded state.

In an embodiment of the invention, there are two hemispherical shell segments, an upper shell segment and the posterior-facing shell segment, and the pressure generating structure is a bulge located on the exterior surface of the posterior-facing cylindrical shell.

In an embodiment of the invention, there are three or more shell segments, including the posterior-facing shell segment, and the pressure generating structure is a reversibly extendible pressure pole which is configured to be retracted within the shell segment when the device is in the collapsed state and extended when the device is in the expanded state.

In an embodiment of the invention, the pressure pole is at least one of extended and retracted by at least one of magnetic and mechanical force.

In an embodiment of the invention, the degree of extension of the pressure pole is controlled by at least one of magnetic field intensity and reversibly locking integral snaps located in the posterior-facing shell segment.

In an embodiment of the invention, the pressure pole is at least one of extended and retracted by a worm gear.

In an embodiment of the invention, the state-changing mechanism includes an actuator connected to a rack by a detachable holder and where the rack is operatively connected to at least one threaded pole by a plurality of cog wheels, wherein the actuator is configured to move coaxially in the holder, and wherein movement of the actuator in a distal direction causes movement of the shell segments towards the expanded state of the device and movement of the actuator in a proximal direction causes movement of the shell segments towards the collapsed state of the device.

In an embodiment of the invention, one of the plurality of cylindrical shells is configured with at least one fender configured to stabilize the fecal incontinence device in an anterior-posterior intra vaginal arrangement.

In an embodiment of the invention, the state-changing mechanism includes a holder, in contact with a central tube having a hinged connection with at least one arm for each of the shell segments, and a puller.

In an embodiment of the invention, the puller has a plurality of pulling rods with bulges that are attached to a slider which also has hinged connection with each arm of the shell segments, wherein when the holder is pushed in a proximal direction, the pulling rods pull the slider over the central tube in a distal direction thus shortening the distance between the slider and the hinged connection, changing the state of the device from the collapsed state to the expanded state.

In an embodiment of the invention, the device further comprises press blocks of an inner rotating mechanism on both sides of the puller wherein the press blocks push the bulges on the pulling rods which causes the pulling rods to rotate, aligning the pulling rods with an opening in the slider, and allowing detachment of the pulling rods from the slider.

There is further provided in aspect of the invention, a fecal incontinence device, comprising: an outer shell cylindrically shaped and rounded on both ends; a plurality of front support arms hingedly attached to the outer shell and configured to anchor the device; a plurality of rear arms hingedly attached to the outer shell and configured to support the device, wherein at least one of the rear arms is further configured to apply rectal pressure; and, a state-changing mechanism configured to transition the device from a collapsed state to an expanded state, wherein the front support arms and the rear arms lie flush to an exterior surface of the outer shell when the device is in the collapsed state.

In an embodiment of the invention, the state-changing mechanism comprises a central activation shaft with tapered surfaces and where each of the front support arms and the rear arms has a free edge in contact with one of the tapered surfaces such that when the shaft is moved proximally the shaft forces the front support arms and the rear arms to rotate around their hinges and transition the device from the collapsed state to the expanded state.

In an embodiment of the invention, the tapered surfaces have a different angle for the rear arms than for the front support arms, resulting in a different range of motion for the rear arms with respect to the front support arms.

In an embodiment of the invention, the device further comprises an applicator including a holder and a pusher, where the pusher moves axially within the holder.

In an embodiment of the invention, the pusher is in contact with the activation shaft such that pushing the pusher distally causes movement of the activation shaft distally, opening the front support arms and the rear arms outwards and into the expanded state.

In an embodiment of the invention, the holder has two sets of snaps situated on grooves at a front end of the device, such that snaps prevent the device from moving distally during insertion of the device into the vagina.

In an embodiment of the invention, the applicator is configured to be rotatable around a longitudinal axis of the device, and wherein the snaps are configured to be bendable by rotation of the applicator, releasing them from the slots and allowing for removal of the applicator.

In an embodiment of the invention, the device further comprises a plurality of locking snaps on the activation shaft that snap into slots on the device and prevent the activation shaft from moving in the distal direction, keeping the front support arms and the rear arms opened and the device in the expanded state.

In an embodiment of the invention, there is a plurality of slots that allow locking of the activation shaft in several positions, thus creating multiple expansions options for the front support arms and the rear arms.

In an embodiment of the invention, there are 3 or more of each of the front support arms and the rear arms.

There is further provided in aspect of the invention, a fecal incontinence device, comprising: a plurality of support arches; and at least one rectum pressing element.

In an embodiment of the invention, the device further comprises a locking mechanism configured to reversibly lock at least one of the plurality of support arches and the at least one rectum pressing element in an open configuration.

There is further provided in aspect of the invention, a fecal incontinence device, comprising: a main body configured for insertion in a sagittal plane of a vagina; a rectum pressing element on the bottom of the main body; and a curved fin opposite the rectum pressing element on the main body.

There is further provided in aspect of the invention, a fecal incontinence device, comprising: at least one set, including, an upper pole element; and a lower pole element attached to the upper pole element, wherein the upper pole element and the lower pole element are configured to move apart with respect to each other to reversibly place the device into an expanded state.

In an embodiment of the invention, the device further comprises a plurality of sets, the sets connected by at least one connection bar.

There is further provided in aspect of the invention, a fecal incontinence device, comprising: a support ring part, configured to stabilize the device in a vagina when expanded; and, a rectal pressing part, configured for reversible attachment to the support ring part and for applying pressure to the rectum when expanded.

There is further provided in aspect of the invention, a fecal incontinence device, comprising: a support ring; an angularly activated rectum pressing element, shaped to anchor the device adjacent and configured to apply pressure to the rectum when in an expanded state.

There is further provided in aspect of the invention, a fecal incontinence device, comprising: a rectum pressing element configured with a bulge to apply pressure to the rectum when the device is in an expanded state; and, an anchoring element, configured with a saddle for cupping a urethra to prevent direct pressure on the urethra when the device is in an expanded state.

In an embodiment of the invention, the device further comprises at least one side stabilizer.

In an embodiment of the invention, the device further comprises a locking mechanism.

In an embodiment of the invention, the device further comprises an applicator.

In an embodiment of the invention, the applicator is configured with a biased handle.

In an embodiment of the invention, the device further comprises a removal string.

In an embodiment of the invention, a removal string is connected to the worm gear and pulling on the string causes the worm gear to transition the device back to the collapsed state.

In an embodiment of the invention, a removal string is connected to the locking snaps such that pulling on the removal string bends the locking snaps inwards and releasing the locking snaps from the slots, transforming the device back to the collapsed state.

In an embodiment of the invention, the device further comprises an outer soft layer.

In an embodiment of the invention, the device is configured to gradually transition from the collapsed state to the expanded state such that the transition may be stopped at a plurality of different expanded device sizes.

There is further provided in an aspect of the invention, a fecal incontinence device, comprising: a plurality of shell segments, which together form an enclosed cylinder with rounded ends in a collapsed state of the device, wherein one of the cylindrical shells is disposed in the device facing a posterior wall of the vagina when the device is inserted into the vagina; a pressure generating structure attached to and abutting the posterior-facing cylindrical shell; and, a state-changing mechanism configured to reversibly transition the device from the collapsed state to an expanded state, wherein the state-changing mechanism includes a puller and a holder, the holder in contact with a central tube having a hinged connection with two equally sized arms for each of the shell segments, except the posterior-facing shell segment which has one arm shorter than the equally sized arms and one arm longer than the equally sized arms, such that when the device transitions to the expanded state, the posterior-facing shell segment expands in an angled relationship to a longitudinal axis of the device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and not necessarily to scale, and are for purposes of illustrative discussion of embodiments of the invention. In this regard, the description taken with the drawings makes apparent to those skilled in the art how embodiments of the invention may be practiced.

In the drawings:

FIGS. 6H-6I are cross-sectional views showing an applicator disconnecting from the 3-piece, cylindrical fecal incontinence device of FIGS. 6A-6B, according to an exemplary embodiment of the invention;

FIGS. 6J-6K are perspective views of a central tube, in locked and released states, respectively, of the 3-piece cylindrical fecal incontinence device of FIGS. 6A-6B, according to an exemplary embodiment of the invention;

FIGS. 6L-6M are cross-sectional views of the central tube, in locked and released states, respectively, of the 3-piece cylindrical fecal incontinence device of FIGS. 6A-6B, according to an exemplary embodiment of the invention;

FIGS. 7A-7B are perspective views showing the magnetic activation of an optional press pole of the 3-piece, cylindrical fecal incontinence device of FIGS. 6A-6B, according to an exemplary embodiment of the invention;

FIGS. 12A-12B are perspective views, collapsed and open, respectively, of a curved fin fecal incontinence device, according to an exemplary embodiment of the invention;

FIG. 12C is an isometric view of the proximal side of the curved fin fecal incontinence device of FIGS. 12A-12B, according to an exemplary embodiment of the invention;

FIGS. 13H-13J are cross-sectional views of the device and applicator of FIGS. 13F-13G showing the expanding mechanism of the applicator, according to an exemplary embodiment of the invention;

FIG. 13K shows an expansion method using the applicator of FIGS. 13F-13G, according to an exemplary embodiment of the invention;

FIGS. 13L-13M are side and close-up views, respectively, of a locking mechanism of the applicator of FIGS. 13F-13G, according to an exemplary embodiment of the invention;

FIGS. 14E-14F are perspective views, collapsed and open, respectively, of the two-part fecal incontinence device with the rectal pressing part applicator, according to an exemplary embodiment of the invention;

FIG. 14G is a perspective view of an open two-part fecal incontinence device of FIGS. 14A-14B, according to an exemplary embodiment of the invention;

FIG. 14H is cross-sectional view of the open two-part fecal incontinence device of FIGS. 14A-14B, according to an exemplary embodiment of the invention;

FIGS. 15A-15B are perspective views, collapsed and open, respectively, of a piston activated fecal incontinence device, according to an exemplary embodiment of the invention;

DESCRIPTION OF SPECIFIC EMBODIMENTS OF THE INVENTION

Figures 1A, 1B:
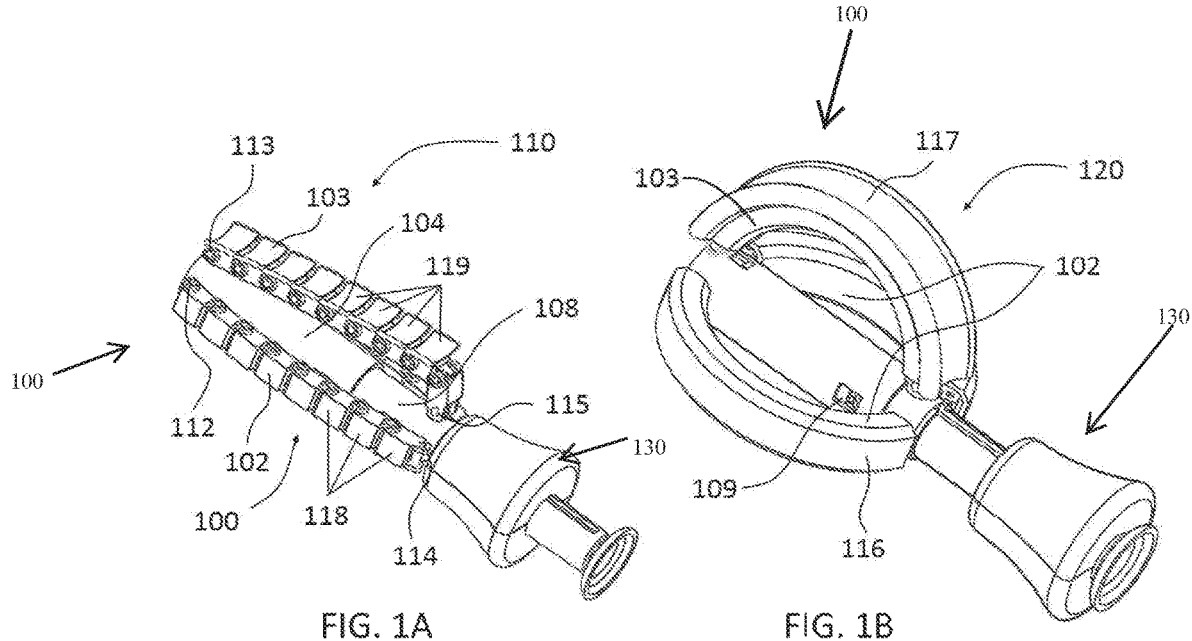
FIGS. 1A-1B are perspective views of a 3-arch fecal incontinence device with applicator, according to exemplary embodiments of the invention.

The present invention, in some embodiments thereof, relates to health care and, more particularly, but not exclusively, to devices and methods for ameliorating fecal incontinence in women.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. It should also be understood that as used herein, "proximal" or "proximally" means closest to the vaginal introitus or in a direction towards the outside of the patient's body and "distal" or "distally" means closest to the cervix or in direction moving further inside the patient's body. Description of devices herein, when referencing proximal or distal directions, is in the context of third person's view of a deployed device in a patient's vagina. For example, the distal end of a device is the end closest to the cervix (farthest into the patient) when the device is inserted into the patient.

FIGS. 1A-1B are perspective views of a 3-arch fecal incontinence device 100 with applicator 130, according to exemplary embodiments of the invention. As shown in FIG. 1A and FIG. 1B, the device 100 is configured to transform from a collapsed state 110 to an expanded state 120. In some embodiments of the invention, the device 100 assumes the collapsed state 110 during storage, insertion and/or removal from a patient's vagina. In some embodiments of the invention, the device 100 assumes the expanded state 120 after insertion to render support to the rectum.

In an embodiment of the invention, the fecal incontinence device 100 comprises at least two side arches 102 and a rectum pressuring element/arch 103. In some embodiments, side arches 102 are configured for anchoring the device bilaterally within the vagina. In some embodiments, the rectum pressuring arch 103 is configured to apply posterior force when the device 100 is deployed in the vagina, thereby pressing the rectum. In some embodiments of the invention, the arches 102, 103 are covered by an elastic material layer 116, 117 (shown in FIG. 1B) that serves as padding to reduce pressure on the vaginal tissue and/or enhance patient comfort.

The arches 102, 103 are connected to an external tube 104 at the distal end of the device 100 and an internal tube 108 at a proximal end of the device 100. In other words, in an embodiment, the top ends (distal ends) 112, 113 of the arches 102, 103 are attached to the external tube 104 and the proximal ends 114, 115 of the arches 102, 103 are attached to an internal tube 108. In some embodiments, the internal tube 108 is coaxially mounted within the external tube 104 to enable telescoping between the tubes 104, 108. In an embodiment of the invention, telescoping means the internal tube 108 slides within the external tube 104 to adjust the overall length of the device 100 and/or the degree of bending of the arches 102, 103. It should be understood that while the tubes 104, 108 are called "tubes" which would imply a cylindrical shape, they are not necessarily cylindrical. For example, external tube 104 may have a square shaped cross-sectional profile.

Figures 2A, 2B:
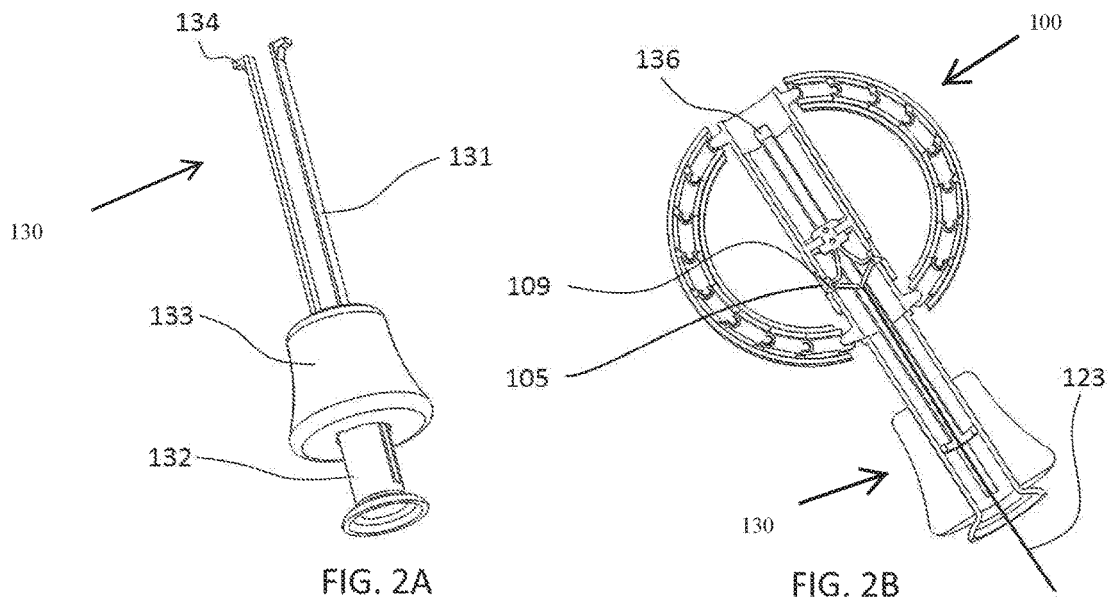
FIG. 2A is a perspective view of the applicator of FIGS. 1A-1B, according to an exemplary embodiment of the invention.
FIG. 2B is a cross-sectional view of the device of FIGS. 1A-1B, according to an exemplary embodiment of the invention.

FIG. 2A is a perspective view of the applicator 130, in accordance with an exemplary embodiment of the invention. In an embodiment of the invention, the applicator 130 is attached to the device 100 and used for insertion of the device 100 into a vagina and/or for transforming the device 100 from the collapsed state 110 (FIG. 1A) into the expanded state 120 (FIG. 1B). In an embodiment of the invention, the applicator 130 comprises a holder 131, a pusher 132 and/or a gripping area 133.

In an embodiment of the invention, the holder 131 is attached to the device 100 by two protruding teeth 134 that are situated in retaining slots 136 in the external tube 104, shown and described in more detail with respect to FIG. 2B. The holder 131 and pusher 132 are configured to allow axial movement of the pusher 132 relative to the holder 131, where the pusher 132 moves axially within the holder 131. Pushing the pusher 132 causes the proximal end of the device 100 to move towards the distal end of the device 100 and the protruding teeth 134 prevent the external tube 104 from moving, thereby shortening its overall length and causing an outward bowing or expansion of the arches 102, 103.

Pressing the pusher 132 situates the internal tube 108 in a position that separates the holder's protruding teeth 134 from the outer tube's retaining slots 136 (leaving the device in situ). In an embodiment of the invention, when the applicator 130 is removed, the removal string's 123 distal end extends outside the vagina (similar to a regular menstrual tampon).

To remove the pessary from the vagina, in an embodiment of the invention, the removal string 123 connected to a snapping element 109 is pulled, thus becoming slightly elongated and narrower, with its 2 arms contracted inwards, thereby releasing the locking mechanism. Unlocking the locking mechanism allows the device 100 to transform from the expanded state 120 back to the collapsed state 110 for easier removal which is achieved by a sustained proximal tension on the removal string 123.

FIG. 2B is a cross-sectional view of the device 100 in the expanded mode 120, according to an exemplary embodiment of the invention. In an embodiment of the invention, the external tube 104 has slots 105 and the internal tube 108 has a snapping element 109 that protrudes from the inner tube 108 wherein the snapping element 109 is configured to be removably inserted into the slots 105. The snapping element 109, shown in FIG. 2B, serves as a locking mechanism by contracting inwards when encountering the external tube 104 (when transforming from the collapsed state 110 to the expanded state 120) and moving back to its original position in the slots 105, thus locking the device 100 in its expanded state and preventing the external tube 104 from returning to its original position (collapsed state 110).

Figure 2C:
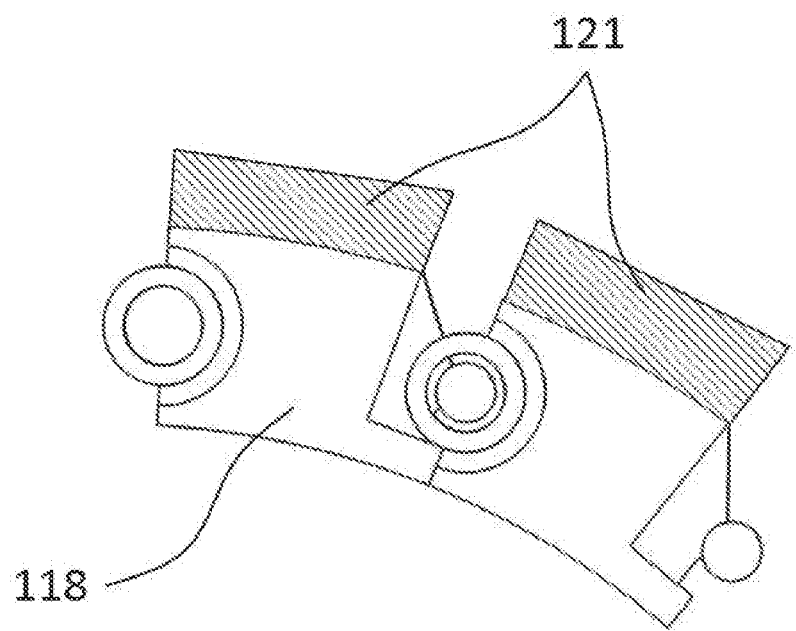
FIGS. 2C-2D are side and perspective views of links of the device of FIGS. 1A-1B, according to exemplary embodiments of the invention.

In an embodiment of the invention, the arches 102, 103 are chainlike, made of several links 118, 119 allowing for arch flexibility, yet stability when locked. FIG. 2C is a detailed view of two links 118 that form the support arches 102, in some embodiments of the invention.

Figure 2D:
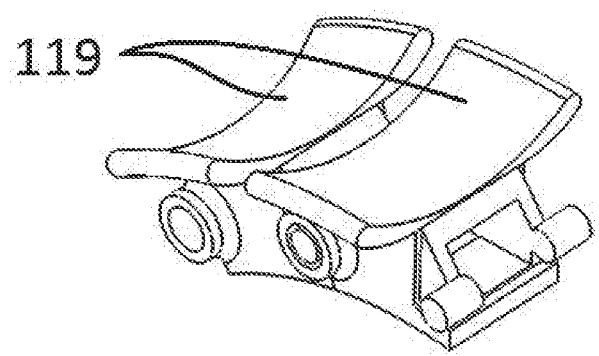

FIG. 2D is a detailed view of two links 119 that form the rectum pressuring arch 103. In an embodiment of the invention, the rectum pressuring arch 103 is configured to stabilize the device 100 with respect to the rectum, for example by being provided with a curved surface which conforms to the natural anatomical features of the posterior wall of the vagina adjacent to the rectum.

In some embodiments of the invention, at least one of the links 118, 119 has a cover 121 for providing protection to the inner surfaces of the vagina and/or enhancing patient comfort.

Figures 3A, 3B:
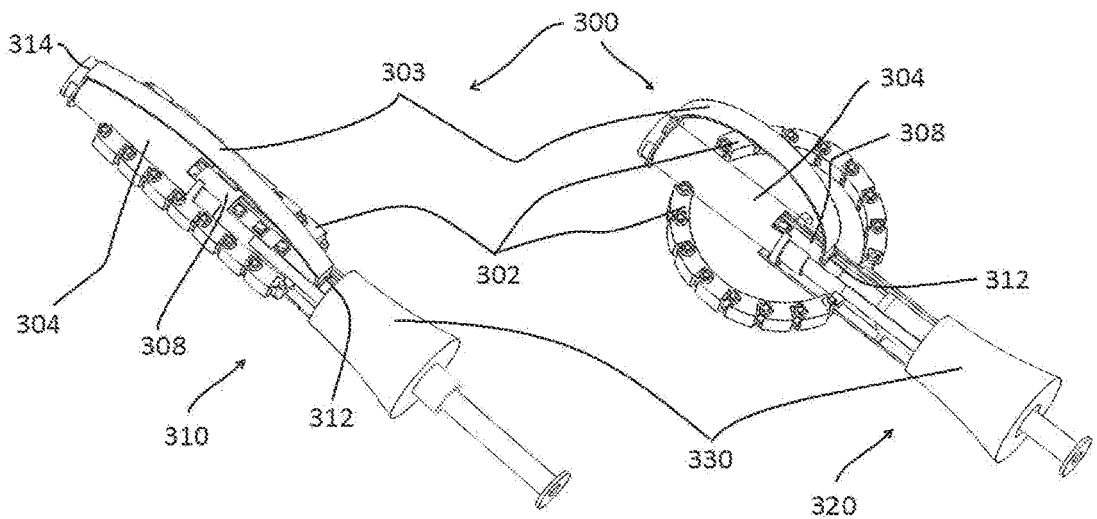
FIGS. 3A-3B are perspective views, collapsed and open, respectively, of a 3-arch fecal incontinence device with a snapping teeth mechanism, according to an exemplary embodiment of the invention.

FIGS. 3A-3B are perspective views, collapsed and open, respectively, of a 3-arch fecal incontinence device 300 with a snapping teeth mechanism, according to an exemplary embodiment of the invention. In some embodiments, the device 300 comprises at least two support arches 302 and a bendable rectal arch 303, which is configured to abut and to apply posterior force on the rectum from within the vagina. In some embodiments, the support arches 302 anchor the device 300 bilaterally within the vagina. An applicator 330 is attached to an external tube 304, in accordance with an exemplary embodiment of the invention. As shown in FIG. 3A and FIG. 3B, the device 300 is configured to transform from a collapsed state 310 to an expanded state 320. In some embodiments of the invention, the device 300 assumes the collapsed state 310 during storage, insertion and/or removal from the vagina. In some embodiments of the invention, the device 300 assumes the expanded state 320 after insertion.

In an embodiment of the invention, a proximal end 312 of the bendable rectal arch 303 is attached to an inner telescopic element 306. A distal end 314 of the bendable rectal arch 303 is attached to an external tube 304. The inner telescopic element 306 is coaxial with the external tube 304 and a support tube 308.

In some embodiments of the invention, proximal ends of the support arches 302 are attached to the support tube 308 and the distal ends of the support arches 302 are attached to the external tube 304.

Figure 3C:
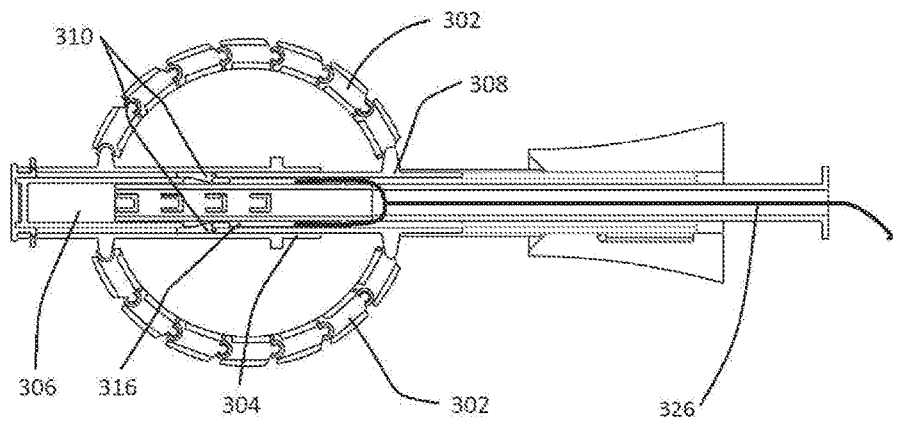
FIG. 3C is a top cross-sectional view of the open 3-arch fecal incontinence device of FIGS. 3A-3B, according to an exemplary embodiment of the invention.

FIG. 3C is a top cross-sectional view of the open 3-arch fecal incontinence device 300, according to an exemplary embodiment of the invention. The support tube 308 has inwards snapping teeth 310, in an embodiment of the invention. A locking tube 316 is positioned coaxially with the external tube 304, support tube and inner telescopic element 306, in an embodiment. The locking tube 316 is situated between the inner telescopic element 306 and the support tube 308. Pushing the support tube 308 in the distal direction snaps the snapping teeth 310 into slots in the locking tube 316, thus locking the support arches 302.

The inner telescopic element 306 can be moved separately inside the locking tube 316 allowing the bendable rectal arch 303 to have a different distance between its proximal end 312 and its distal end 314 than that of the support arches 302. The inner telescopic element 306 has a snapping element 324, in an exemplary embodiment of the invention. Pushing the inner telescopic element 306 in the distal direction snaps the snapping element 324 into slots in the locking tube 316, thus locking the rectal arch 303.

Figure 3D:
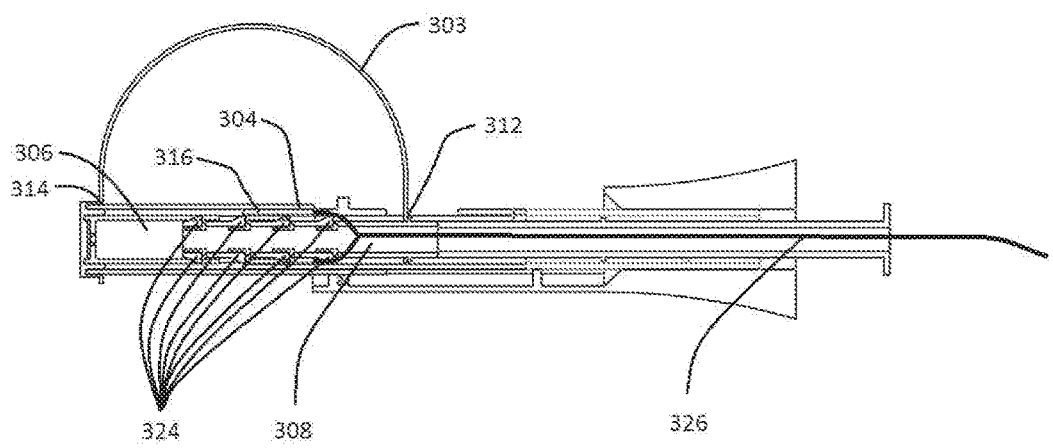
FIG. 3D is a side view of the open 3-arch fecal incontinence device of FIGS. 3A-3B, according to an exemplary embodiment of the invention.

In another embodiment of the invention, the bendable rectal arch 303 can have multiple snapping elements 324, such as shown in FIG. 3D. In some embodiments, the bendable rectal arch 303 can be locked at various distances between its proximal end 312 and its distal end 314 allowing the user to control the distance between its proximal end 312 and its distal end 314, thereby controlling the force applied on the rectum.

Figure 3E:
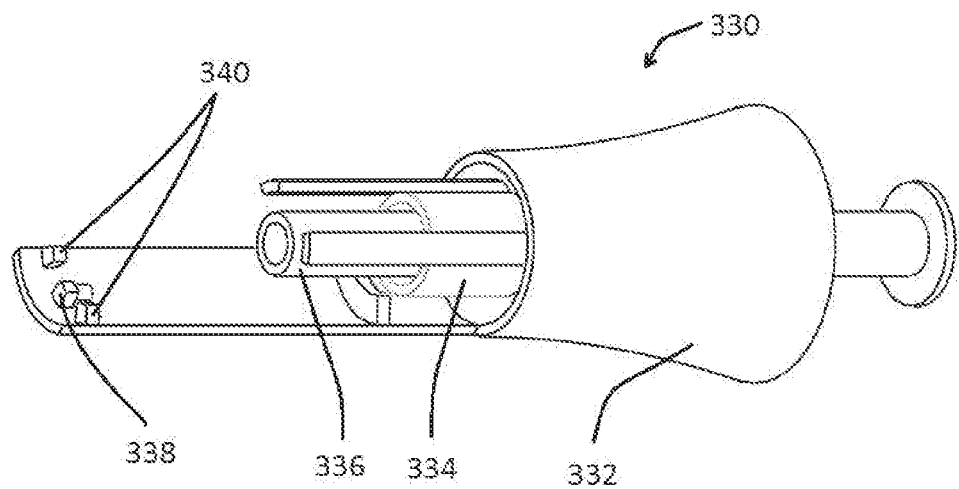
FIGS. 3E-3F are perspective and cross-sectional views, respectively, of the applicator of the open 3-arch fecal incontinence device of FIGS. 3A-3B, according to an exemplary embodiment of the invention.
Figure 3F:
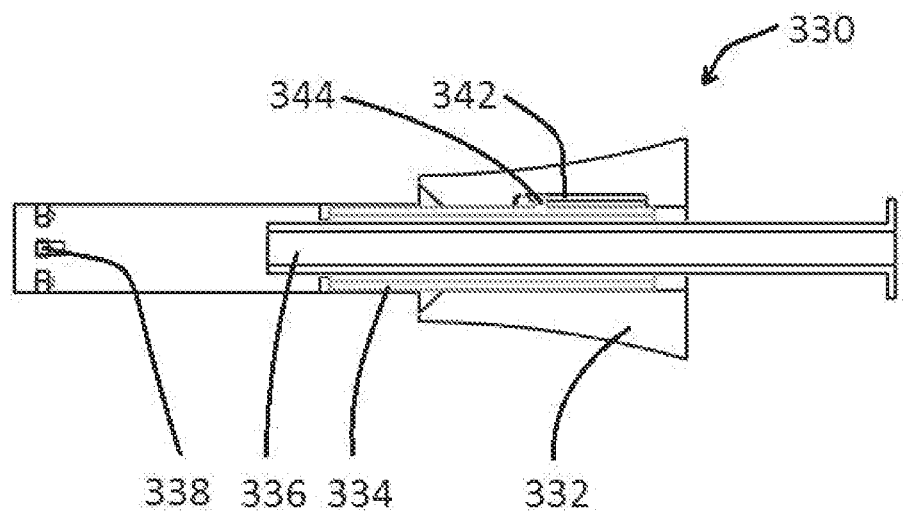

FIGS. 3E-3F are perspective and cross-sectional views, respectively, of the applicator 330 of the open 3-arch fecal incontinence device 300, according to an exemplary embodiment of the invention. In an embodiment of the invention, the applicator 330 is attached to the device 300 and used for insertion the device 300 into a vagina and for transforming the device 300 from the collapsed state 310 (FIG. 3A) into the expanded state 320 (FIG. 3B). In an embodiment of the invention, the applicator 330 comprises a holder 332, a support pusher 334 and a rectal support pusher 336. In some embodiments, the holder 332 is attached to the device 300 by protruding teeth 338 with holding pins 340 that function as retaining walls to counter on the outer tube 304 and prevent it from moving during compression.

The holder 332, support pusher 334 and rectal support pusher 336 are configured to allow axial movement of the pushers 334, 336 relative to the holder 332 and to each other, where the pushers 334, 336 move axially within the holder 332. In an embodiment of the invention, pushing the rectal support pusher 336 causes the proximal end of the rectal arch 303 to move towards the distal end, thereby shortening its overall length and causing an outward bowing or expansion of the rectal support arch 303. At the same time, the rectal support pusher 336 also pushes the support pusher 334 towards the distal end of the device 300, thereby shortening the overall length causing an outward bowing or expansion of the support arch 302.

In the holder 332 there is a leading canal 342 that directs the movement of the support tube 308 via a leading pin 344 on the support pusher. After the support arches are fully locked, the leading canal 342 causes rotation of the support pusher 344, this rotation disconnects the support pusher 344 from the rectal support pusher 346 and allows for the rectal support pusher to continue moving distally (without further pushing the locked support arches 302).

Once the support arches 302 are locked, and the rectal support arch 303 is also locked, the applicator 330 is released from the device 300 by rotation of the applicator 330. The rotation causes disconnection between the protruding teeth 338 and protrusions on the external tube 304. In an embodiment of the invention, when the applicator 330 is removed, a removal string's 326 proximal end extends outside the vagina (similar to a regular menstrual tampon), the removal string 326 shown in FIGS. 3C and 3D.

To remove the device 300 from the vagina, in an embodiment of the invention, the removal string 326 connected to the locking tube 316 is pulled, thus bending the snapping teeth 320 and snapping element 324 inwards, releasing the locking mechanism. Unlocking the locking mechanism allows the device 300 to transform from the expanded state 320 back to the collapsed state 310 for easier removal which is achieved by a sustained proximal tension on the removal string 326.

Figures 4A, 4B:
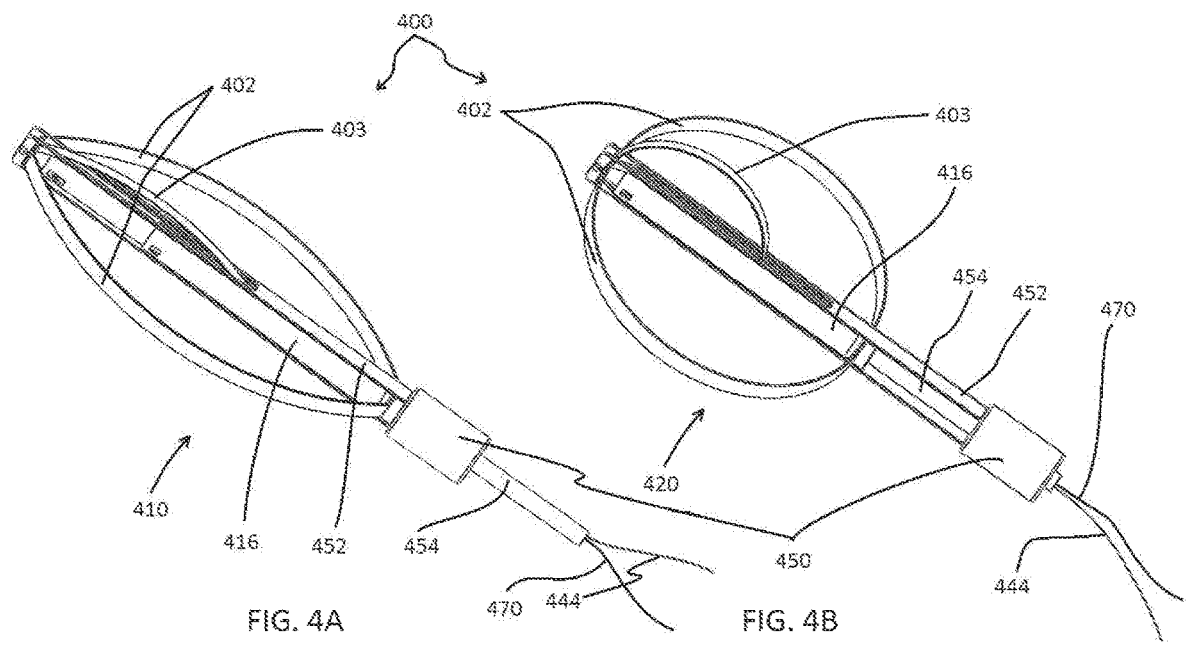
FIGS. 4A-4B are perspective views, collapsed and open, respectively, of a 3-arch fecal incontinence device with a pen toggle mechanism, according to an exemplary embodiment of the invention.

FIGS. 4A-4B are perspective views, collapsed and open, respectively, of a 3-arch fecal incontinence device 400 with a pen toggle mechanism, according to an exemplary embodiment of the invention. In an embodiment of the invention, the device 400 comprises at least two support arches 402 and a bendable rectal arch 403. In some embodiments of the invention, the device 400 assumes the collapsed state 410 during storage, insertion and/or removal from the vagina. In some embodiments of the invention, the device 400 assumes the expanded state 420 after insertion. The device comprises at least two bendable support arches 402 used for anchoring the device bilaterally within the vagina, and a third bendable rectal arch 403 used for applying posterior force, thereby pressing the rectum.

Figure 4C:
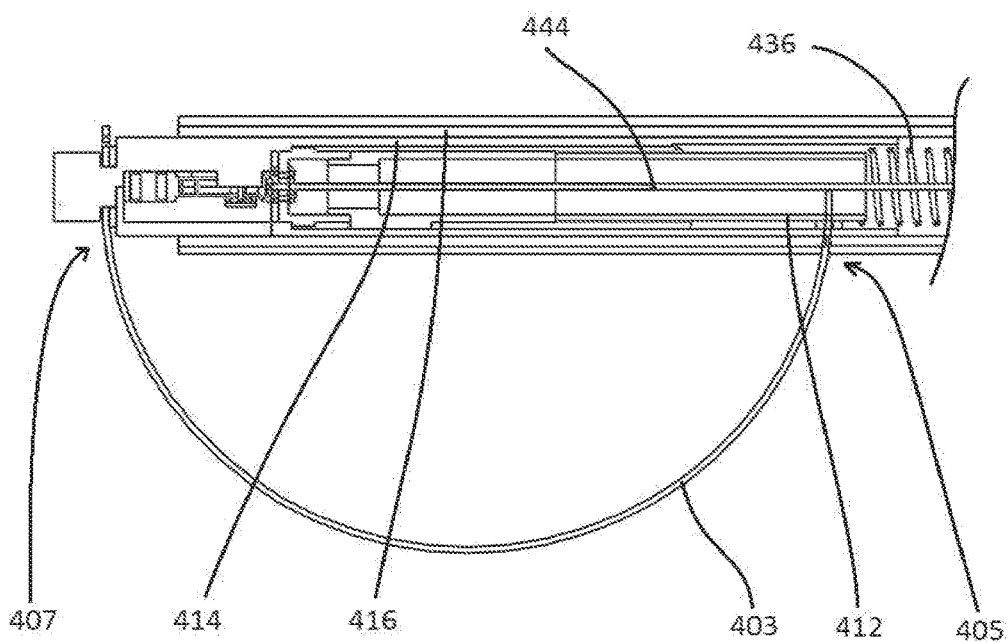
FIG. 4C is a cross-sectional view of the 3-arch fecal incontinence device with a pen toggle mechanism of FIGS. 4A-4B, according to an exemplary embodiment of the invention.

FIG. 4C is a cross-sectional view of the 3-arch fecal incontinence device 400 with a pen toggle mechanism (shown in more detail in FIG. 4D), according to an exemplary embodiment of the invention. In an embodiment of the invention, FIG. 4C shows an activation mechanism of the bendable rectal arch 403. A distal end 405 of the bendable rectal arch 403 is attached to an inner telescopic element 412. A proximal end 407 of the bendable rectal arch 403 is attached to the inner support tube 414. In some embodiments, the inner telescopic element 412 is coaxial with the inner support 414 and external support tube 416. In an embodiment of the invention, proximal ends of the support arches 402 are attached to the external support tube 416 and distal ends are attached to the inner support tube 414.

Figure 4D:
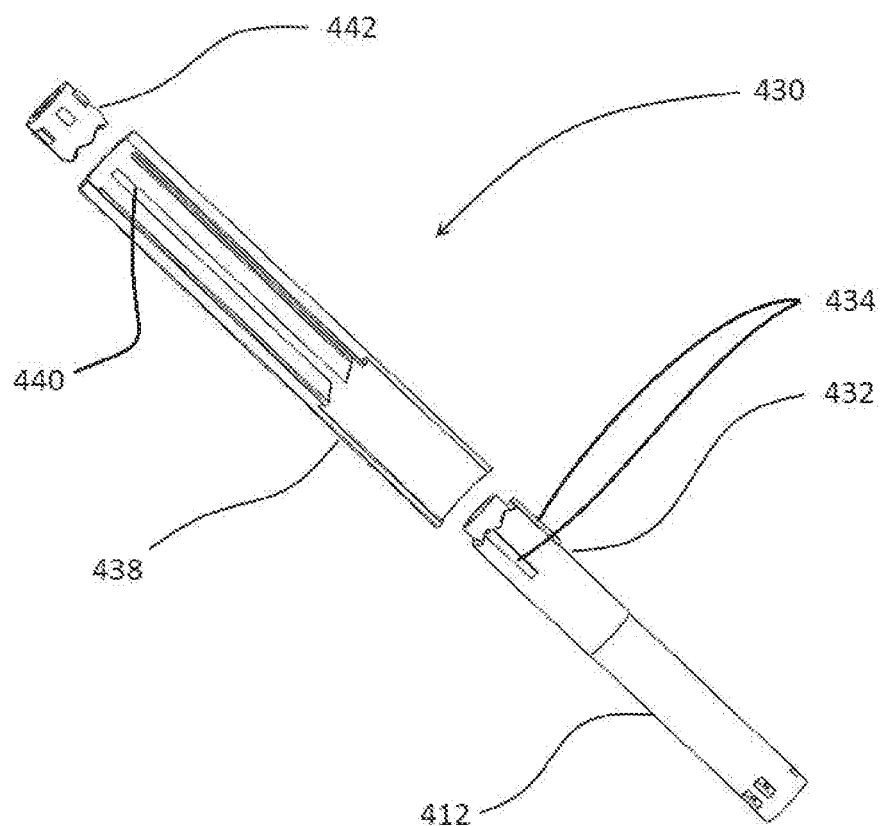
FIG. 4D is a partially exploded view of a pen toggle mechanism of the 3-arch fecal incontinence device with a pen toggle mechanism of FIGS. 4A-4B, according to an exemplary embodiment of the invention.

FIG. 4D is an exploded view of a "pen toggle mechanism" 430 used for toggling of the inner telescopic element 412 between two or more positions. The toggle mechanism is composed of a rotator tube 432 with guide fins 434 contacting the inner telescopic element 412, a spring 436 (FIG. 4C) that presses the inner telescopic element against the rotator tube 432, mechanism tube 438 with guiding slots 440 and a crowned toggle 442 connected to a pulling string 444 (FIG. 4C). The inner telescopic element 412, rotator tube 432 and mechanism tube 438 are coaxial. Pushing the inner telescopic element 412 in the distal direction causes the rotator tube 432 to move in the distal direction as well. Pulling the rotator tube 432 in the proximal direction (by a pull of the pulling string 444) causes the inner telescopic element 412 to move in the proximal direction as well.

When pulling the pulling string 444, the crowned toggle 442 slides within the mechanism tube's slots 440 and pushes the rotator tube 432 in the proximal direction, thus the inner telescopic element 412 is pushed in the proximal direction. Pushing the inner telescopic element in the proximal direction compresses the spring 436. Once the rotator tube 432 exits the mechanism tube's slots 440 (but not completely exiting the mechanism tube 438) it rotates due to the crowned toggle 442 rim's shape to a position in which the guide fins 434 are able to slide within the mechanism tube's slots 440. Thus, the rotator tube 432 and inner telescopic element 412 are pushed by the spring 444 causing an outward bowing or expansion and of the bendable rectal arch 403. A second pull of the pulling string 444 causes the crowned toggle 442 to slide within the mechanism tube's slots 440 and pushes the rotator tube 432 in the proximal direction, thus the inner telescopic element 412 is pushed in the proximal direction. Pushing the inner telescopic element in the proximal direction compresses the spring 436. Once the rotator tube 432 exits the mechanism tube's slots 440 (but not completely exiting the mechanism tube 438) it rotates due to the crowned toggle 442 rim's shape to a position in which the guide fins 434 are unable to slide within the mechanism tube's slots 440. Thus, the rotator tube 432 and inner telescopic element 412 remain in their initial position.

Toggling the "pen toggle mechanism" enables switching the bendable rectal arch 403 between activated and not activated positions (pressing the rectum and providing relief of the rectal pressure) while the support arches 402 remain in the expanded state, keeping the device 400 in place and allowing patient undisturbed defecation without the need to replace the device.

In an embodiment of the invention, an array of different length mechanism tube slots 440 can be used to obtain more than two locking positions for the third telescopic element, allowing control of the pressure on the rectum.

Figures 4E, 4F:
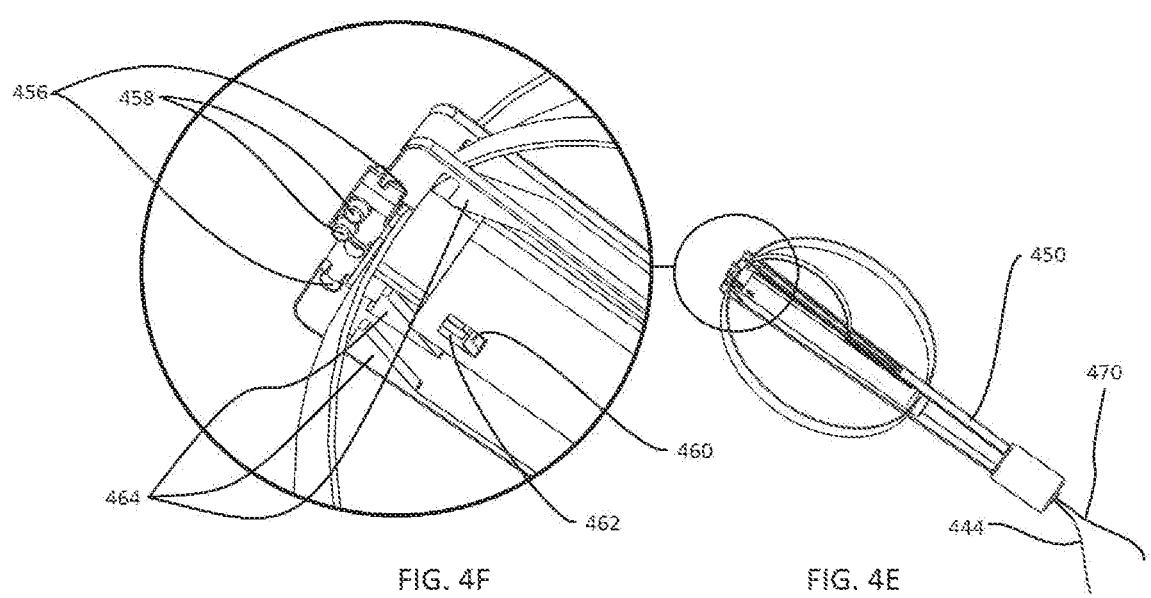
FIGS. 4E-4F are perspective and close-up views, respectively, of an interface between the applicator and the 3-arch fecal incontinence device with a pen toggle mechanism of FIGS. 4A-4B, according to an exemplary embodiment of the invention.

FIGS. 4E-4F are perspective and close-up views, respectively, of an interface between the 3-arch fecal incontinence device 400 and the applicator 450 that is used to insert the device into the vagina and to transfer it from its collapsed state 410 to its expanded state 420, according to an exemplary embodiment of the invention. The applicator 450 consists of a holder 452 and a pusher 454. The holder 452 is attached by snapping elements 456 to snapping pins 458 on the device's 400 distal side.

The pusher 454 is in contact with the external support tube 416 (FIG. 4A). When the pusher 454 is pushed the external support tube 416 is moved distally until the device 400 reaches its expanded state 420 where a locking mechanism 460 snaps into slots 462 in the external support tube 416. A further push of the pusher 454 brings the external support tube 416 distal rim to contact with release diagonal protrusions 464 on the holder 452 pressing the arms of the holder 452 outwards and disconnecting the holder's snapping elements 456 from the snapping pins 458. The applicator 450 is then pulled out of the vagina leaving the device 400 inside the vagina and a removal string 470 (separate of the toggle mechanism pulling string 444) with its proximal end out of the vagina.

The distal end of the removal string 470 is connected to the locking mechanism 460. At the end of the device use the patient pulls the removal string 470 deforming the locking mechanism 460 thus causing it to snap out of the slots 462, releasing the device from its expanded state 420 and allowing it to transfer back to its collapsed state 410. A further pull of the removal string removes the device out of the vagina.

Figure 4G:
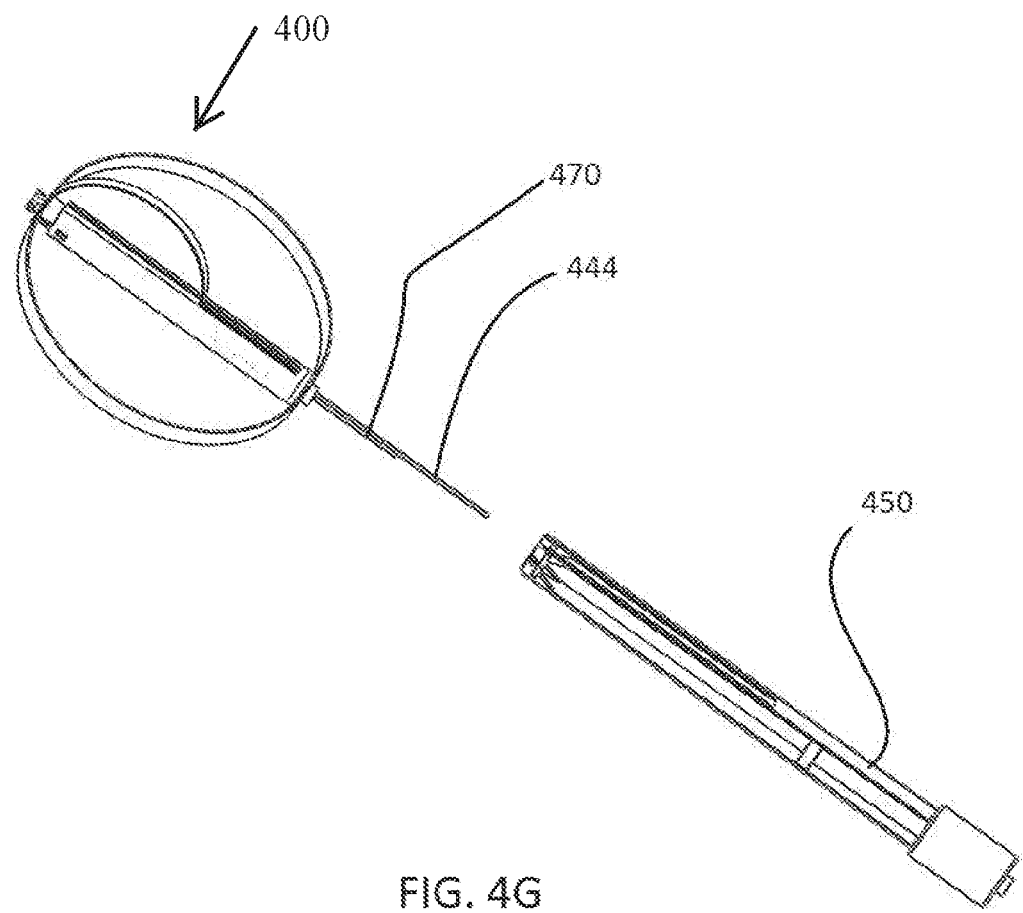
FIG. 4G is a perspective view showing a deployed, open 3-arch fecal incontinence device with a pen toggle mechanism, according to an exemplary embodiment of the invention.

FIG. 4G is a perspective view showing a deployed, open 3-arch fecal incontinence device 400 separated from the applicator 450 after deployment.

Figure 5A:
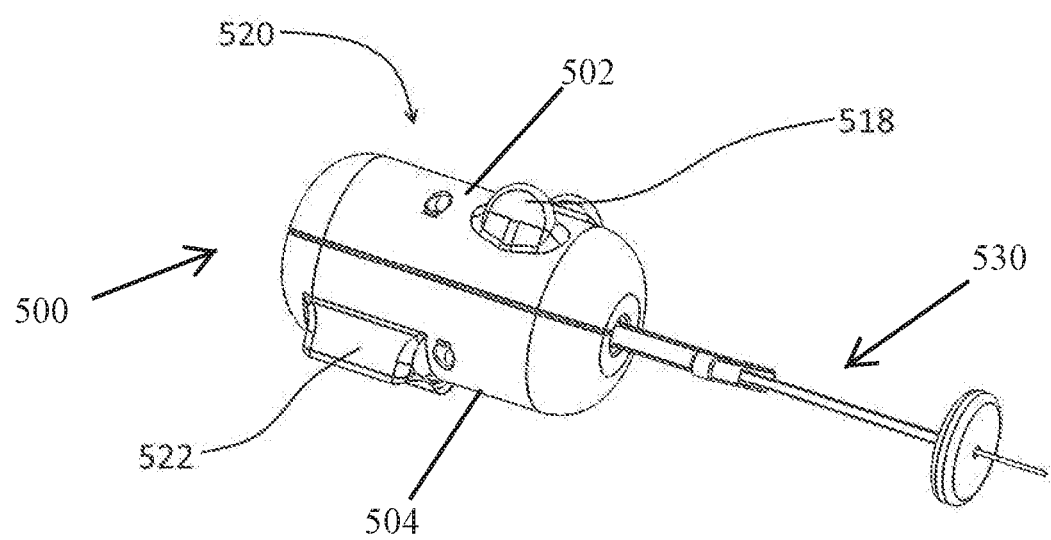
FIG. 5A is a perspective view of a cylindrical fecal incontinence device with an applicator, according to an exemplary embodiment of the invention
Figure 5B:
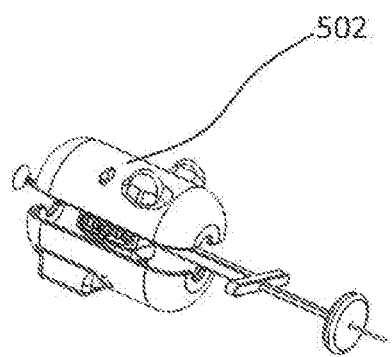
FIGS. 5B-5C are perspective, partially exploded views of the cylindrical fecal incontinence device with an applicator of FIG. 5A, according to an exemplary embodiment of the invention.
Figure 5C:
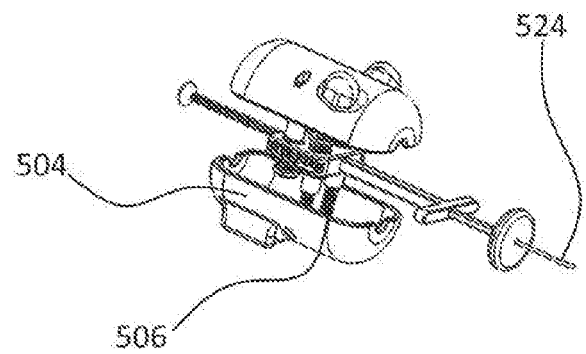

FIG. 5A is a perspective view of a cylindrical fecal incontinence device 500 with an applicator 530, according to an exemplary embodiment of the invention. In an embodiment of the invention, the device 500 comprises two half cylindrical shells 502, 504 held by threaded poles 506 (shown and described with respect to FIG. 5C). In an embodiment of the invention, the applicator 530 is attached to the device 500 and used for insertion of the device 500 into a vagina and for transforming the device 500 from the collapsed state 520 (FIG. 5A) into the expanded state (FIGS. 5B-5C). In some aspects of the invention, the device 500 is inserted into the vagina in its closed configuration 520, where the two shells 502, 504 form a tubular/cylindrical shape with rounded ends (FIG. 5A) and is expanded to render treatment.

The upper shell 502 serves to support the device against the vaginal anterior wall and may have fenders 518 (FIG. 5A) to further stabilize it in an anterior-posterior intra vaginal arrangement. The lower shell 504 serves as a rectal pressure unit and may have a bulge 522 (FIG. 5A) to locate and stabilize it against the rectum and the posterior vaginal wall. Both shells may have an outer soft layer to cushion against vaginal walls.

In another embodiment of the invention the upper shall 502 may comprise of a plurality of segments that open in different directions.

Figure 5D:
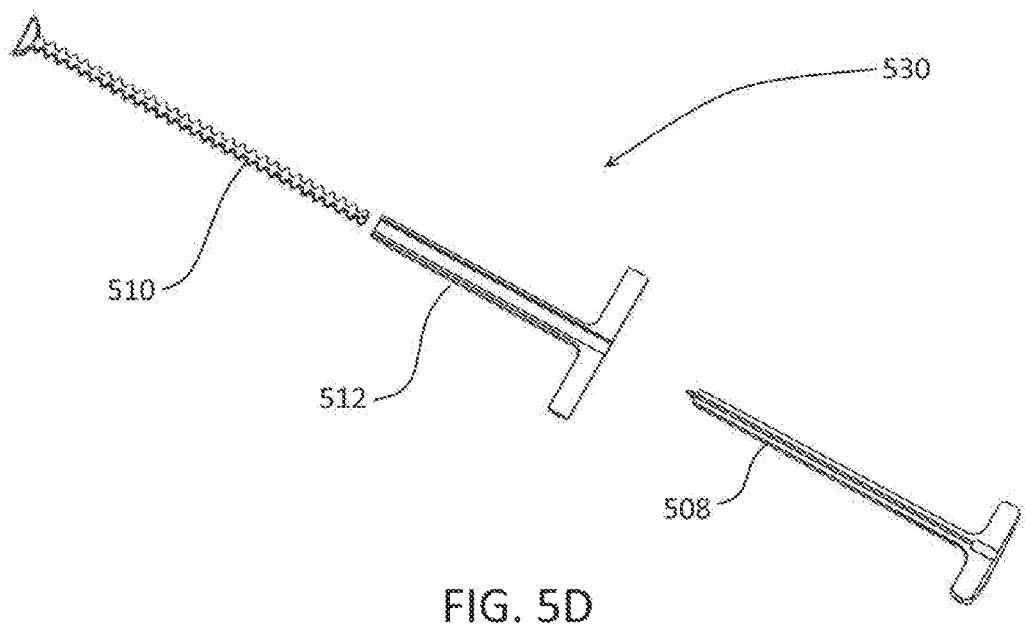
FIG. 5D is a partially exploded view of an applicator used with the cylindrical fecal incontinence device of FIG. 5A, according to an exemplary embodiment of the invention.
Figure 5E:
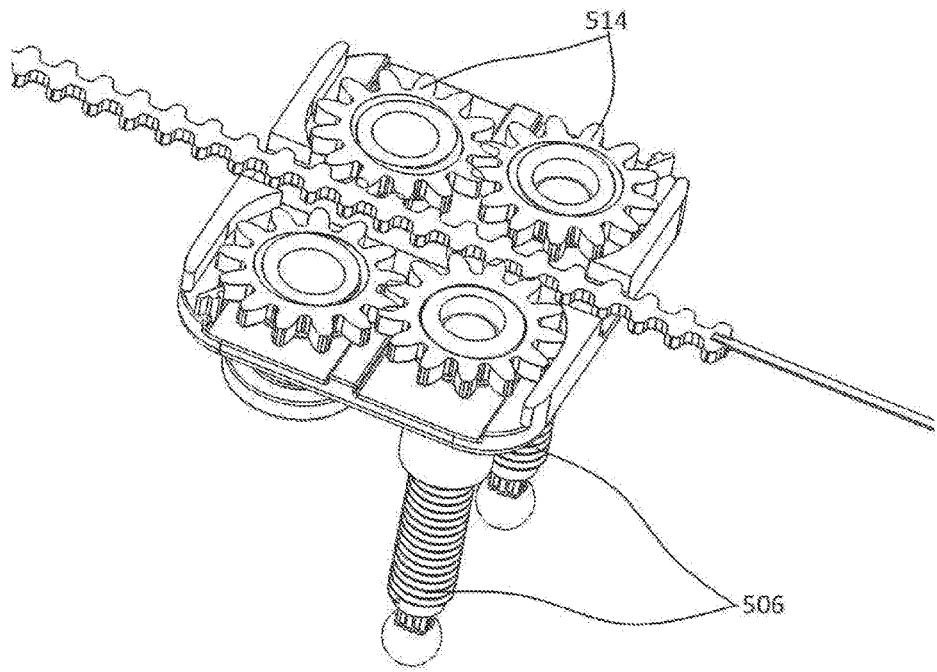
FIG. 5E is a close-up, perspective view of a cog wheel assembly and a rack of the cylindrical fecal incontinence device of FIG. 5A, according to an exemplary embodiment of the invention.

FIG. 5D is a partially exploded view of the applicator 530 used with the cylindrical fecal incontinence device 500, according to an exemplary embodiment of the invention. In an embodiment of the invention, the applicator 530 comprises an actuator 508 connected to a rack 510 by way of a detachable holder 512. The actuator 508 can move coaxially within the detachable holder 512. Pushing the actuator 508 in the distal direction causes movement of the rack 510 in the distal direction. Linear movement of the rack 510 is transformed to rotation of internal cogwheels 514 (FIG. 5E) in contact with the rack 510. Rotation of the cog wheels 514 causes the threaded poles 506 to move in a vertical direction (anterior-posterior) thus gradually increasing (if the rack is moved distally) or decreasing (if the rack is moved proximally) the distance between the two half cylindrical shells 502, 504.

Figure 5F:
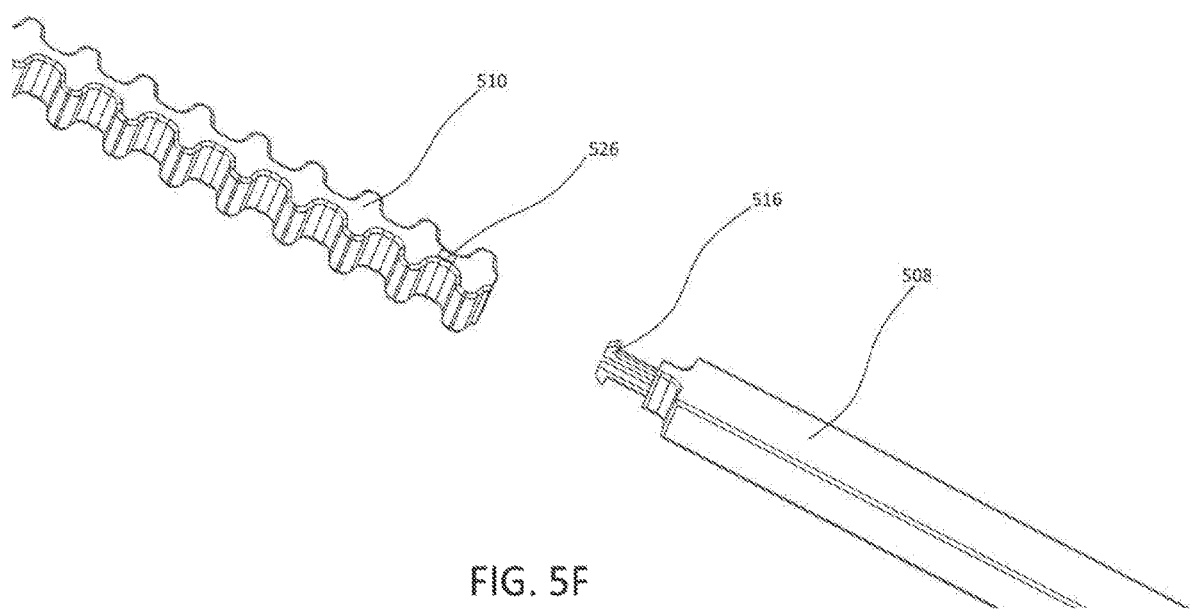
FIG. 5F is a close-up, perspective view of the interface of a rack and an actuator of the cylindrical fecal incontinence device of FIG. 5A, according to an exemplary embodiment of the invention.

FIG. 5F is a close-up, perspective view of the interface of the rack 510 and the actuator 508 of the cylindrical fecal incontinence device 500, according to an exemplary embodiment of the invention. On the distal end of the actuator 508 there is a snapping element 516. The snapping element 516 snaps into slots 526 in the rack 510, thus keeping the rack 510 and actuator 508 connected.

In an embodiment of the invention after device deployment, the holder 512 is removed together with the actuator 508. When pulling the holder 512 in the proximal direction the snapping element 516 bends inward, thus releasing the actuator 508 from the rack 510.

In an embodiment of the invention a removal string's 524 (FIG. 5C) distal end is attached to the rack 510 and its proximal end hangs out of the actuator 508. Removing the actuator 508 and holder 512 leaves the proximal end of the removal string 524 hanging out of the vagina.

Pulling the removal string 524 in the proximal direction will pull the rack 510 in the proximal direction and will cause rotation of the cog wheels 514 in a direction that will cause vertical movement of the shells 502, 504 towards each other, returning the device 500 to it collapsed state 520 (FIG. 5A) for removal from the vagina.

Figures 6A, 6B:
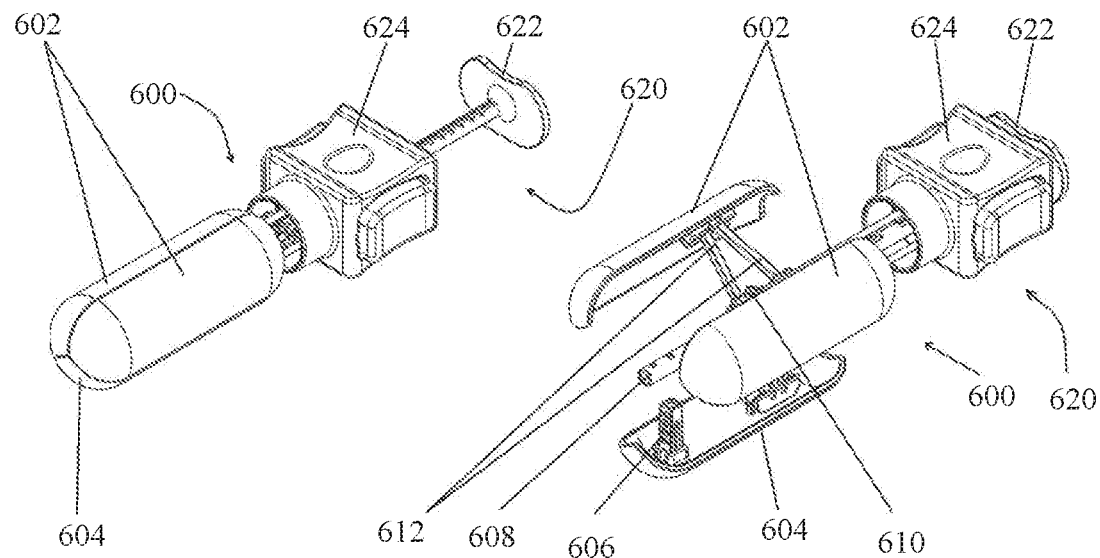
FIGS. 6A-6B are perspective views, collapsed and open, respectively, of a 3-piece, cylindrical fecal incontinence device, according to an exemplary embodiment of the invention.

FIGS. 6A-6B are perspective views, collapsed and open, respectively, of a 3-piece, cylindrical fecal incontinence device 600, according to an exemplary embodiment of the invention. In an embodiment of the invention, the device 600 has a cylindrical shape which is comprised of three or more segments 602, 604. The bottom (posterior) cylindrical segment 604 is configured with a rectal pressure generating pole 606 near its distal end. As with other embodiments described herein, the device 600 (FIG. 6A) is closed during storage insertion and removal and it is expanded (FIG. 6B) following deployment. In an embodiment of the invention, the device expands gradually and may be stopped at any of several sizes, as desired, for example to fit the patient's vagina and/or to render effective amelioration of fecal incontinence. In some embodiments of the invention, posterior pressure is generated by device 600 by at least one of two mechanisms, from the volume filling nature of the three or more segments 602, 604 and also the pressure generating pole 606, described elsewhere herein.

Figure 6C:
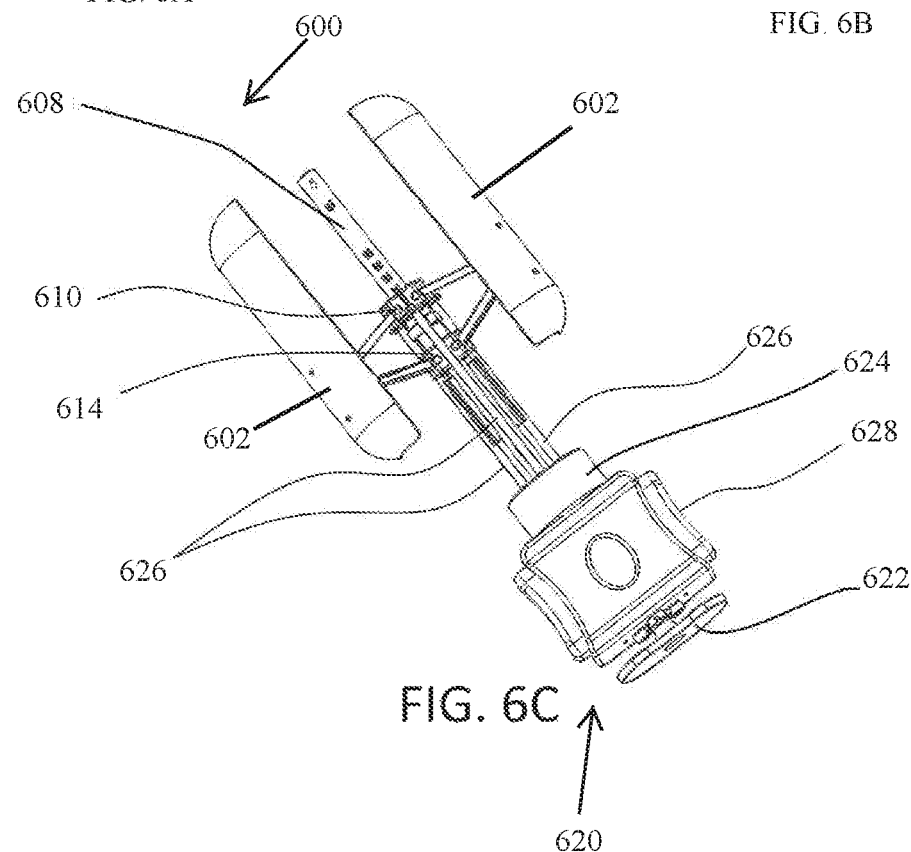
FIG. 6C is an isometric view of the 3-piece, cylindrical fecal incontinence device of FIGS. 6A-6B, according to an exemplary embodiment of the invention.

FIG. 6C is an isometric view of the device 600 with two segments 602 shown. In an embodiment of the invention, the applicator 620 is attached to the device 600 and used for insertion of the device 600 into a vagina and/or for expanding the device 600. The applicator 620 includes a holder 622 and a puller 624. The holder 622 is in contact with a central tube 608 having a hinged connection 614 with at least one arm 612 for each of the segments 602, 604.

Figure 6D:
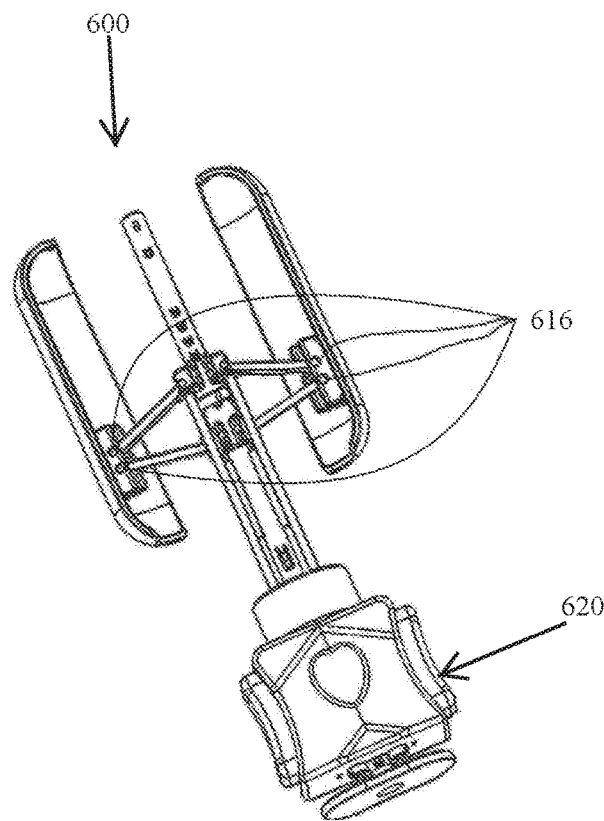
FIG. 6D is a partial, cross-sectional view of the 3-piece, cylindrical fecal incontinence device of FIGS. 6A-6B, according to an exemplary embodiment of the invention.
Figures 6E, 6F, 6G:
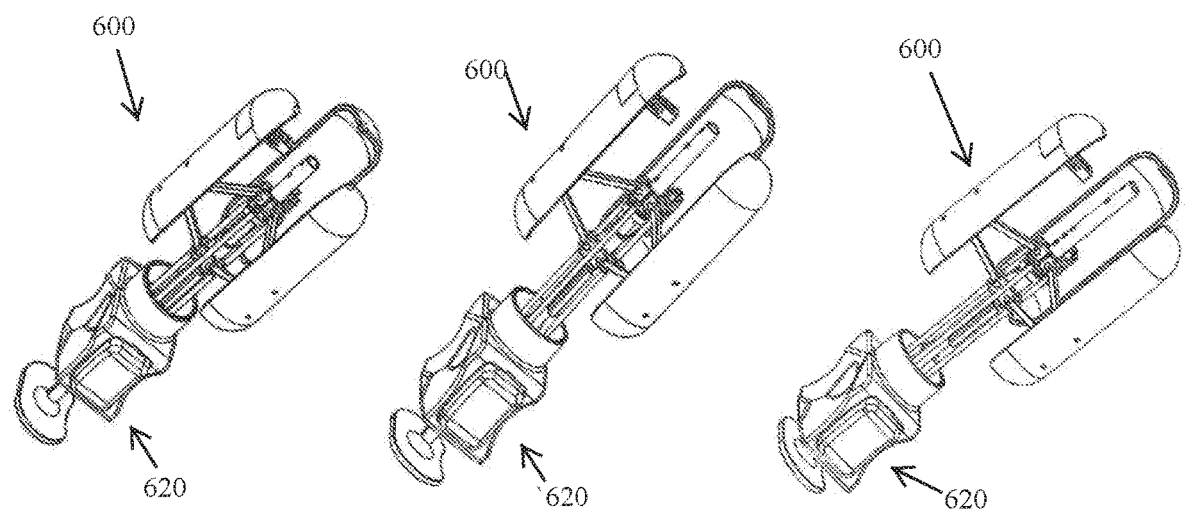
FIGS. 6E-6G are perspective views showing the progression of expansion of the 3-piece, cylindrical fecal incontinence device of FIGS. 6A-6B, according to an exemplary embodiment of the invention.

In an embodiment of the invention, the puller 624 has three pulling rods 626 that are attached to a slider 610 which also has hinged connection with at least one arm 612 for each of the cylindrical segments 602, 604. When the holder 622 is pushed in the proximal direction the pulling rods 626 pull the slider 610 over the central tube 308 in the distal direction thus shortening the distance between the slider 610 and the hinged connection 614. Since each set of arms 612 is (rotationally) connected to a cylindrical segment 602, 604 in hinged connections 616 (FIG. 6D), the angle between the arms is getting smaller causing the cylindrical segments 602, 604 to distance from the central tube 608 and thus gradually expand the device 600, such as shown in FIGS. 6E-6G.

FIGS. 6H-6I are cross-sectional views showing the applicator 620 disconnecting from the 3-piece, cylindrical fecal incontinence device 600, according to an exemplary embodiment of the invention. In an embodiment of the invention, on both sides of the puller 624 there are press blocks 628 of an inner rotating mechanism. When pushed inwards, the press blocks 628 push bulges 629 on the pulling rods 626 which cause the pulling rods 626 to rotate. Rotation of the pulling rods 626 brings their bent proximal ends to alignment with opening in the slider 610, thus allowing detachment from the slider 610 and allowing for the removal of the applicator 620.

FIGS. 6J-6K are perspective views and FIGS. 6L-6M are cross-sectional views of the central tube 608, the slider 610 and the lock ring 634 in locked and released states, respectively. Removal of the device 600 from the vagina is carried out by pulling a removal string 632 connected to the lock ring 634 with openings 619. The lock ring 634 prevents the slider 610 from moving proximally over the central tube 608 (which would cause device collapse) by supporting the central tube's snaps 609 (FIG. 6L). The removal string 632 is connected to the lock ring 634 at the side connection holes 636. The side connection holes 636 are not aligned with the removal string's 632 exit holes 638 from the central tube 608. Pulling of the removal string 632 causes the connection holes 636 and exit holes 638 to align therefor rotating the lock ring 634. When the lock ring 634 rotates the openings 619 are aligned with the snaps 609 (FIG. 6M), thus the slider 610 is no longer prevented from moving proximally over the central tube 608 and the device 600 returns to it collapsed state (FIG. 6A).

In an embodiment of the invention shown in FIGS. 7A-7B, the press pole 606 of device 600 is activated externally by a magnetic power source 700. A control on the stroke of the press pole 606 can be achieved by regulating the magnetic field intensity. The press pole 606 is locked by integral snaps on the bottom cylindrical segment 604. Removal of the press pole 606 is achieved by reversing the magnetic field of the magnetic power source 700.

Figures 8A, 8B:
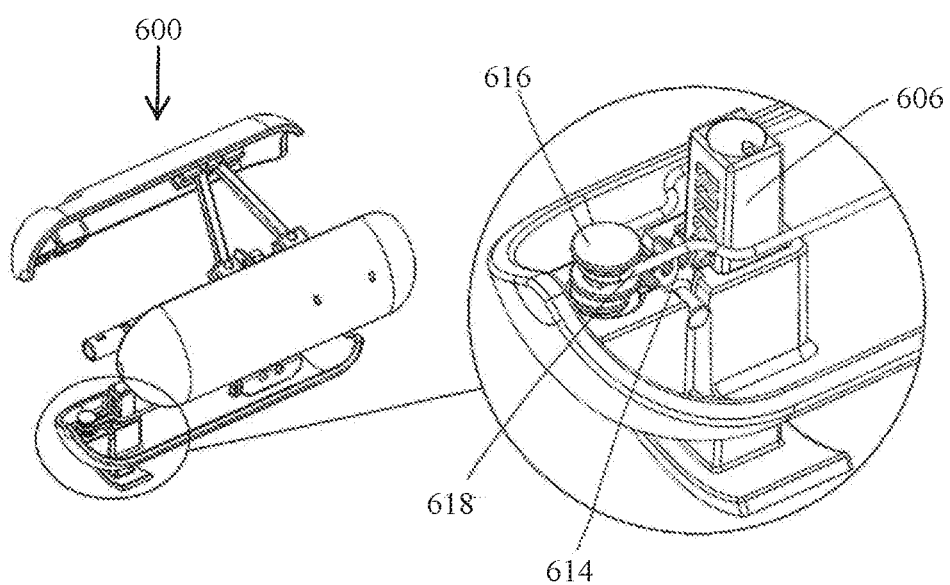
FIGS. 8A-8B are perspective and close-up views, respectively, of an optional mechanically-activated press pole of the 3-piece, cylindrical fecal incontinence device of FIGS. 6A-6B, according to an exemplary embodiment of the invention.

FIGS. 8A-8B are perspective and close-up views, respectively, of an optional mechanically-activated press pole 606 of the device 600, according to an exemplary embodiment of the invention. In an embodiment of the invention shown, the press pole 606 of device 600 is constructed as a linear gear rack and is moved open/closed by rotation of a gearwheel 814. The gearwheel may be rotated using a worm gear 816. The worm gear 816 by nature serves also as a locker of the gearwheel 814. A string 818 is connected and wrapped around the worm gear 816, pulling of the string 818 causes rotation of the worm gear 816 thus opening/closing of the press pole 606 (depending on which end of the string 818 is pulled). In some embodiments, another string (protruding through the vaginal orifice) but in a loop fashion (as opposed to the single string is designed to close the device 600 for removal.

Figures 9A, 9B:
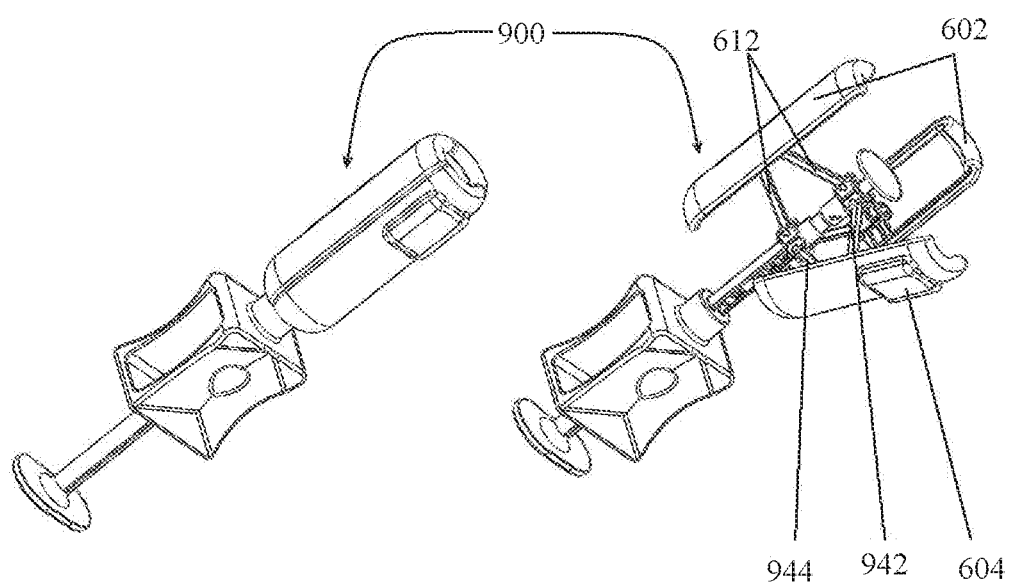
FIGS. 9A-9B are perspective views, collapsed and open, respectively, of a biased, 3-piece, cylindrical fecal incontinence device, according to an exemplary embodiment of the invention.

FIGS. 9A-9B are perspective views, collapsed and open, respectively, of a biased, 3-piece, cylindrical fecal incontinence device 900 (largely based on device 600, with some variances), according to an exemplary embodiment of the invention. In an embodiment, arms 942, 944 that connect the bottom (posterior) cylindrical segment 604 to the central tube 608 and slider 610 are longer and shorter (respectively) than the arms 612 that connect the other cylindrical segments 602. Thus, during the expansion of device 900, the movement of the bottom (posterior) cylindrical segment 604 away from the central axis is of gradually increasing angle (FIG. 9B) with respect to the longitudinal axis of the device, thereby directly applying pressure on the rectum. The cylindrical segments 602, 604 may have an outer soft layer to cushion the vaginal walls.

Figure 10A:
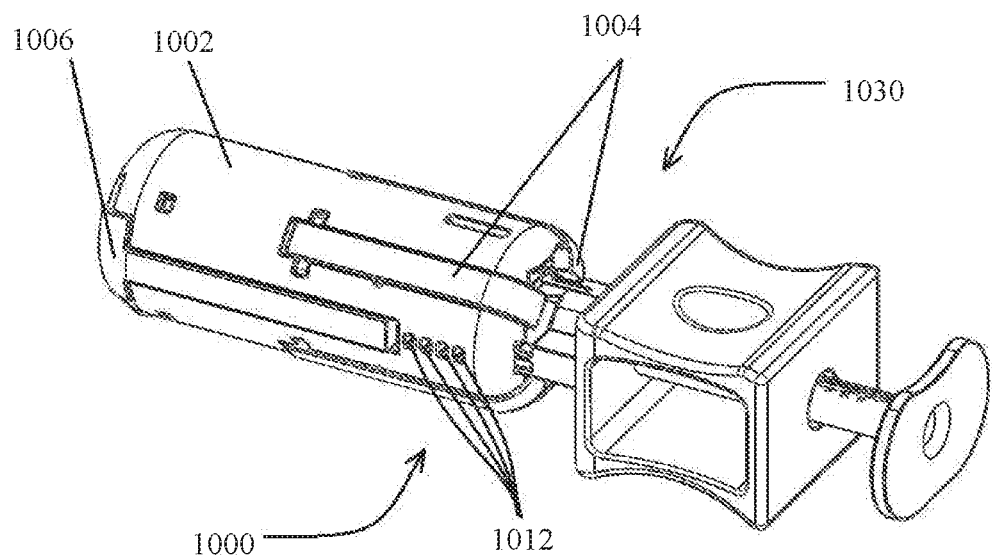
FIGS. 10A-10B are perspective views, collapsed and open, respectively, of a hinged arm fecal incontinence device, according to an exemplary embodiment of the invention.
Figure 10B:
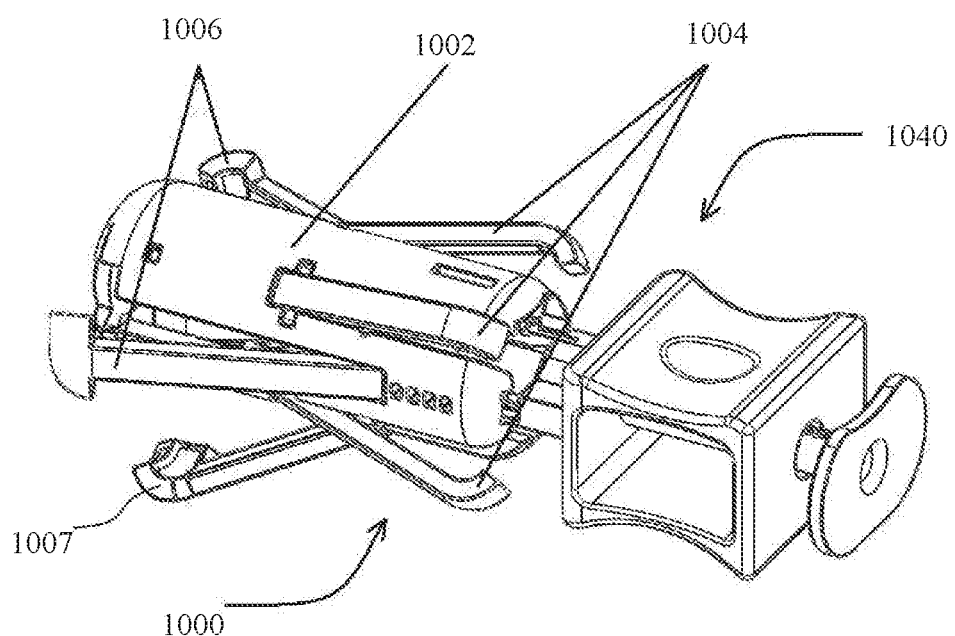

FIGS. 10A-10B are perspective views, collapsed 1030 and open 1040, respectively, of a hinged arm fecal incontinence device 1000, according to an exemplary embodiment of the invention. In an embodiment of the invention, the device 1000 is constructed of an outer cylindrical shell 1002 and a plurality of hinged arms. There are two groups of arms: front support arms 1004 and rear arms 1006, 1007. The front support arms 1004 serve to anchor and/or support the device 1000 in the vagina. The device 1000 may have 2, 3, 4 or more front support arms 1004. At least one of the rear arms 1007 is configured to apply pressure on the rectum, while the other rear arms 1006 are configured to support the device 1000 in the vagina. The device 1000 may have 2, 3, 4 or more rear arms 1006, 1007.

Figure 11A:
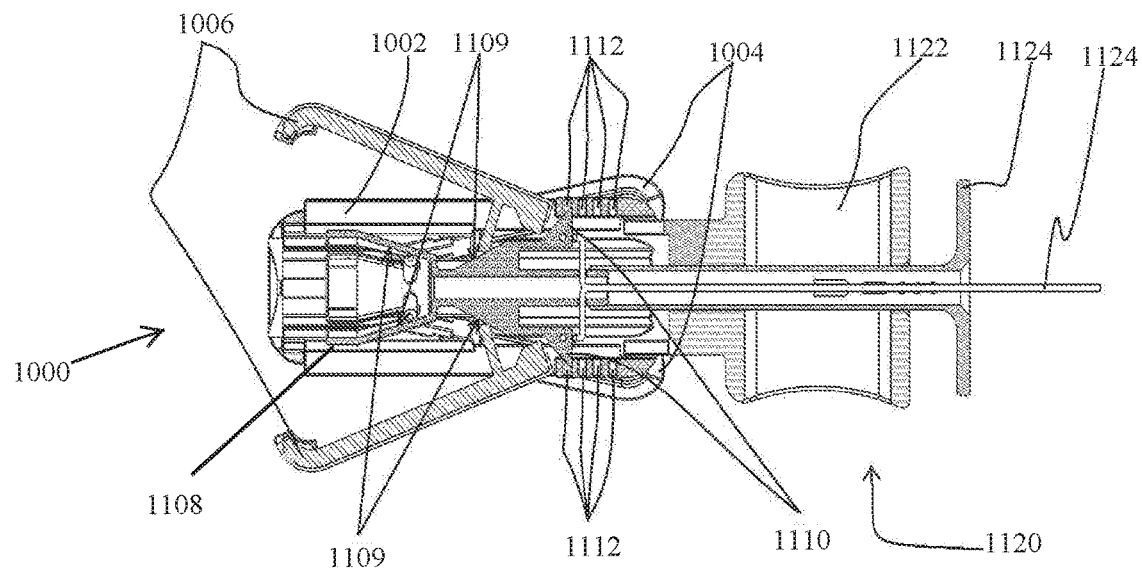
FIGS. 11A-11B are top and side cross-sectional views, respectively, of the hinged arm fecal incontinence device of FIGS. 10A-10B, according to an exemplary embodiment of the invention.

FIG. 11A is a top, cross-sectional view of the device 1000 in its expanded state. The device 1000 has a central activation shaft 1108 with tapered surfaces 1109. Each of the hinged arms (both rear support arms 1006 and front arms 1004) has a free edge in contact with one of the tapered surfaces 1109. When the shaft 1108 is moved proximally it forces the hinged arms to rotate around their hinges and stretch their free edges outwards. The tapered surfaces 1109 may have a different angle for the rear supporting arms 1006 than the angle for the front arms 1004, resulting in a different range of motion for the arms.

In an embodiment of the invention, the tapered surface 1109 which is in contact with the rear arm 1007 that is aimed to press the rectum has a different angle with regards to the tapered surfaces 1109 contacting the other rear arms 1006, to enable larger range of motion for this arm 1007.

Figure 11B:
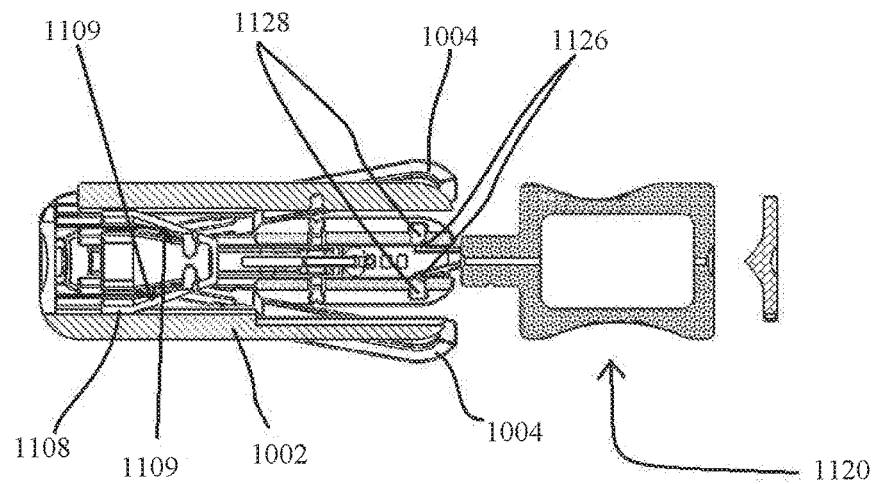

FIG. 11B is a side cross section view of the device 1000 in its expanded state. In an embodiment of the invention, the applicator 1120 is attached to the device 1000 and used for insertion of the device 1000 into a vagina and for transforming the device 1000 from the collapsed state 1030 (FIG. 10A) into the expanded state 1040 (FIG. 10B). The applicator 1120 includes a holder 1122 and a pusher 1124 (FIG. 11A). The holder 1122 and pusher 1124 are configured to allow axial movement of the pusher 1124 relative to the holder 1122, where the pusher 1124 moves axially within the holder 1122. The holder 1122 has two sets of snaps 1126 (shown in FIG. 11B) situated on grooves 1128 in the front end of the device 1000, these snaps 1126 prevent the device 1000 from moving distally during insertion. The pusher 1124 is in contact with the activation shaft 1108. Pushing the pusher 1124 distally causes movement of the activation shaft 1108 distally thus opening the rear and front support arms (1006 and 1004) outwards.

On the activation shaft 1108 there are two locking snaps 1110 that snap into slots 1112 on the device 1000 and preventing the activation shaft 1108 from moving in the distal direction thus keeping the support arms (1004, 1006) opened outwards.

In an embodiment of the invention there is a plurality of slots 1112 that allow locking of the activation shaft 1108 in several positions, thus creating multiple expansions options of the rear and front support arms (1006 and 1004).

The applicator snaps 1126 are bent inwards and released from the grooves 1128 by rotation of the applicator 1120 (around the device's 1000 longitudinal axis) allowing for applicator 1120 removal. Once the applicator 1120 is removed the distal end of the removal string 1014 is left hanging out of the vagina. To remove the device 1000 from the vagina, in an embodiment of the invention, the removal string 1114 connected to the locking snaps 1110 is pulled, thus bending them inwards, thereby releasing the locking snaps from the slots 1112. Releasing of the locking snaps 1110 allows the device 1000 to transform from the expanded state 1040 back to the collapsed state 1030 for easier removal which is achieved by a sustained proximal tension on the removal string 1114.

FIGS. 12A-12B are perspective views, collapsed 1220 and open 1230, respectively, of a curved fin fecal incontinence device 1200, according to an exemplary embodiment of the invention.

FIG. 12C is a perspective illustration of the device 1200 within a vagina 1201, in accordance with an exemplary embodiment of the invention. In an embodiment of the invention, a main body of the device 1200 is positioned on the sagittal plane of the patient's vagina, traversing the space between the rectum and the urethra, while applying pressure on the rectum 1202 and not obstructing the urethra 1203. The bottom of the device 1200 is configured with a rectum pressing element 1204, shaped like a curved fin, which also prevents the device 1200 from rotating. On the top of the device 1200 there is a urethra supporting fin 1206 configured to further anchor the device 1200, for example by situating in natural crevices in the vaginal anatomy, and/or is configured to prevent direct pressure on the urethra 1203, for example by being curved.

In an embodiment of the invention, the device 1200 is generally configured to occupy the sagittal plane of a vagina such that the rectum pressing element 1204 abuts the rectum from inside the vagina, while the urethra supporting fin 1206 is located adjacent to the urethra from inside the vagina. While the device 1200 is generally shown in a circular shape when expanded in FIGS. 12B, 12D-12E, it should be understood that the main body of the device could be just about any shape which is capable of positioning the rectum pressing element 1204 and the urethra supporting fin 1206 suitably for rendering fecal incontinence treatment. As examples, the main body of the device 1200 could be ovoid, prismatic, quadrilateral, multi-sided, and the like, when expanded/deployed in the vagina. Similar rationale applies to other devices described herein, for example, as shown and described with respect to FIGS. 14A-14H, 15A-15B, and 16A-16C.

Like with some or all of the other devices described herein, in some embodiments of the invention, the device 1200 assumes the collapsed state 1220 during storage, insertion and removal. In some embodiments of the invention, the device 1200 assumes the expanded state 1230 after insertion.

Figure 12D:
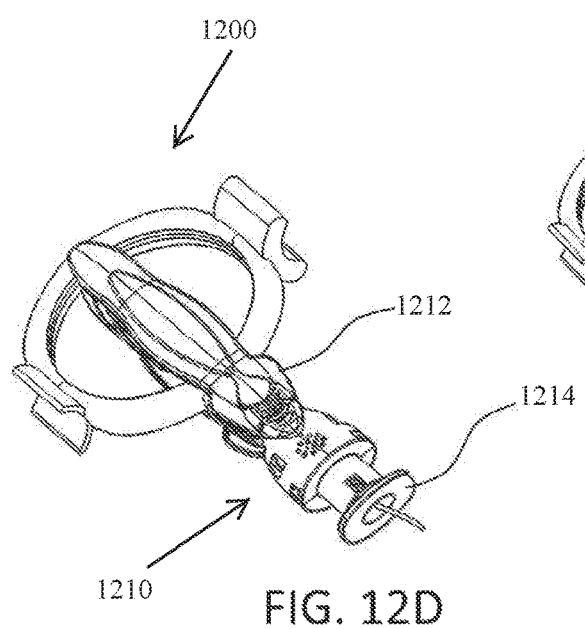
FIGS. 12D-12E are perspective views of the curved fin fecal incontinence device of FIGS. 12A-12B expanded and separated from an applicator, respectively, according to an exemplary embodiment of the invention.
Figure 12E:
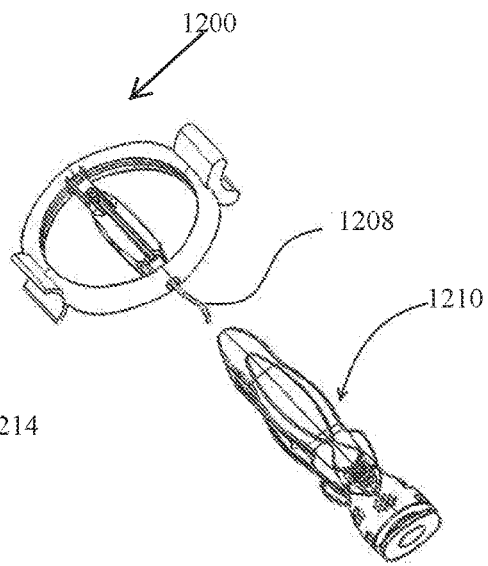

FIGS. 12D-12E are perspective views of the curved fin fecal incontinence device 1200 expanded and separated from an applicator 1210, respectively, according to an exemplary embodiment of the invention. In an embodiment of the invention, the applicator 1210 is attached to the device 1200 and used for insertion of the device 200 into a vagina and/or for transforming the device 1200 from the collapsed state 1220 (FIG. 12A) into the expanded state 1230 (FIG. 12B). In an embodiment of the invention, the applicator 1210 comprises a holder 1212 and a pusher 1214. The holder 1212 and pusher 1214 are configured to allow axial movement of the pusher 1214 relative to the holder 1212, where the pusher 1214 moves axially within the holder 1212. Pushing the pusher 1214 causes the proximal end of the device 1200 to move towards the distal end of the device 1200, thereby shortening its overall length and causing an outward expansion of the rectum pressing element 1204 and the fins 1206.

In an embodiment of the invention, when the applicator 1210 is removed a removal string's 1208 proximal end extends outside the vagina (similar to a conventional menstrual tampon).

Figure 13A:
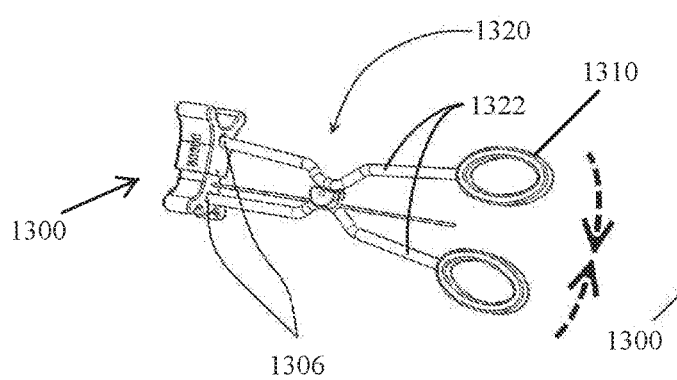
FIGS. 13A-13B are perspective views, collapsed and open, respectively, of an expanding bi-polar fecal incontinence device with an applicator, according to an exemplary embodiment of the invention.
Figure 13B:
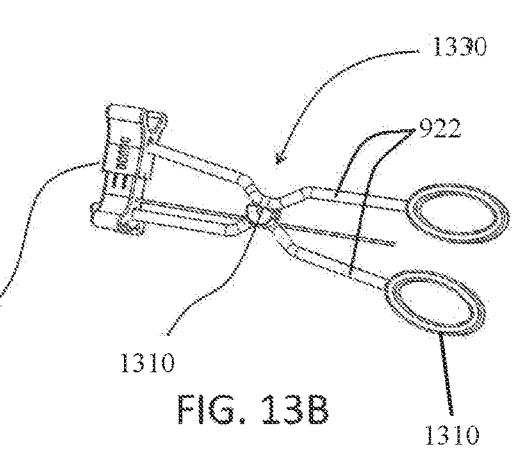

FIGS. 13A-13B are perspective views, collapsed 1320 and open 1330, respectively, of an expanding bi-polar fecal incontinence device 1300 with an applicator 1310, according to an exemplary embodiment of the invention. In an embodiment of the invention, the device 1300 comprises two telescopic elements: an upper pole 1303 and a lower pole 1301, shown in more detail in FIG. 13C. In some embodiments of the invention, the device 1300 assumes the collapsed state 1320 during storage, insertion and/or removal. In some embodiments of the invention, the device 1300 assumes the expanded state 1330 after insertion.

Figure 13C:
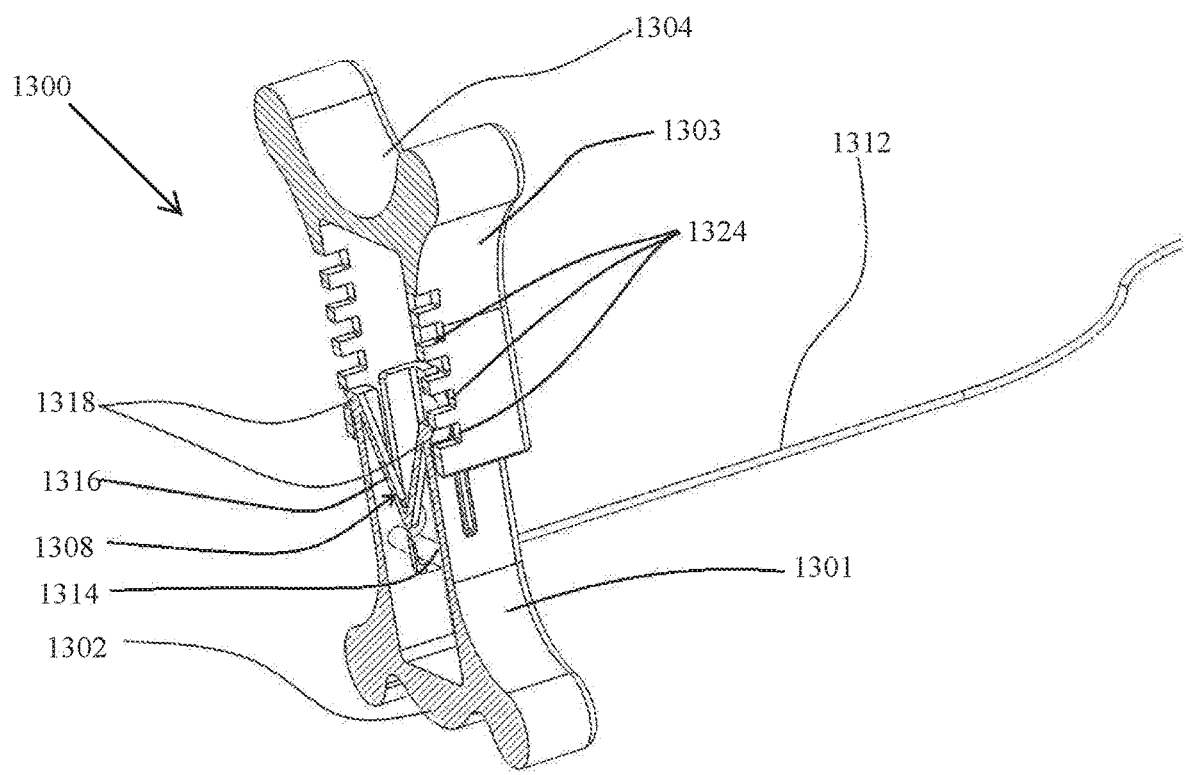
FIG. 13C is a perspective view of the expanding bi-polar fecal incontinence device of FIGS. 13A-13B, according to an exemplary embodiment of the invention.

FIG. 13C is a perspective view of the expanding bi-polar fecal incontinence device 1300, according to an exemplary embodiment of the invention. In an embodiment of the invention, the device 1300 is positioned in a sagittal plane (i.e. antero-posterior position). where the device extend between the urethra and bladder in front and the rectum at the back) and configured for applying pressure on the rectum and not obstructing the urethra. For example, on the bottom of the lower pole 1301 there is a rectum pressing element 1302 that also prevents the device 1300 from rotating. On the top of the upper pole 1303 there are curved fins 1304 further anchoring the device 1300 and the curvature avoids direct pressure on the patient's urethra.

In an embodiment of the invention, the applicator 1310 is attached to the device 1300 through deployment holes 1306 and used for insertion the device 1300 into a vagina and/or for transforming the device 1300 from the collapsed state 1320 (FIG. 13A) into the expanded state 1330 (FIG. 13B). The applicator 1310 is made of two handles 1322 rotationally connected at a common axis (like scissors). Pressing the applicator handles 1322 toward each other pushes the upper pole 1303 away from the lower pole 1301 thereby increasing the overall height (defined as the axis between the rectum and the urethra) of the device 1300.

In an embodiment of the invention there is a locking mechanism 1308 within the lower pole 1301. The locking mechanism 1308 has snaps 1318 that snap into slots 1324 in the upper pole 1303 and thus prevent the device from transforming back from the expanded state to the collapsed state.

In an embodiment of the invention there is a plurality of slots 1324 allowing multiple snapping positions for the snaps 1318. Thus, the device 1300 may attain different heights.

Figures 13D, 13E:
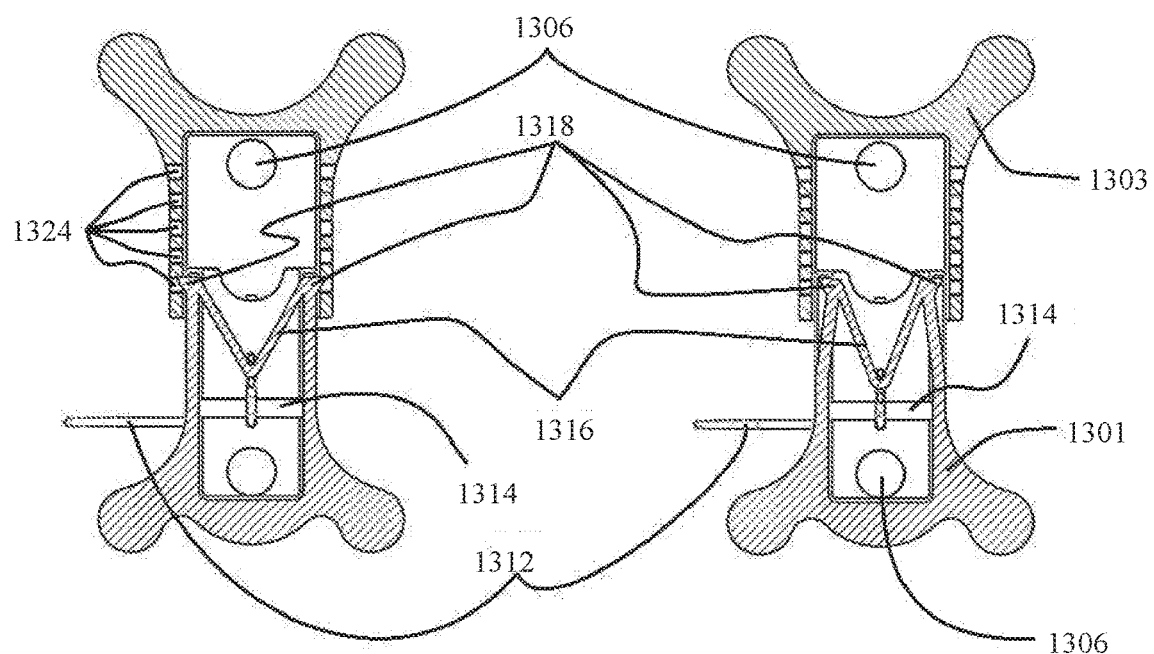
FIGS. 13D-13E are cross-sectional views, before and after pulling a removal string, respectively, of the expanding bi-polar fecal incontinence device of FIGS. 13A-13B, according to an exemplary embodiment of the invention.

FIGS. 13D-13E are cross-sectional views, before and after pulling a removal string 1312, respectively, of the expanding bi-polar fecal incontinence device 1300, according to an exemplary embodiment of the invention. In an embodiment of the invention, when the applicator 1310 is removed, a proximal end of the removal string 1312 extends outside the vagina (similar to a conventional menstrual tampon). The removal string 1312 is connected to the locking mechanism 1308, bends over a pulley 1314 and gets to the outside of the lower pole 1301 through a hole. Pulling of the removal string 1312 causes the locking mechanism bridge 1316 to twist and the locking mechanism snaps 1318 to bend inwards thus releasing the lock between the lower pole 1301 and the upper pole 1303 and allowing the device 1300 to return to its collapsed state 1320.

Figures 13F, 13G:
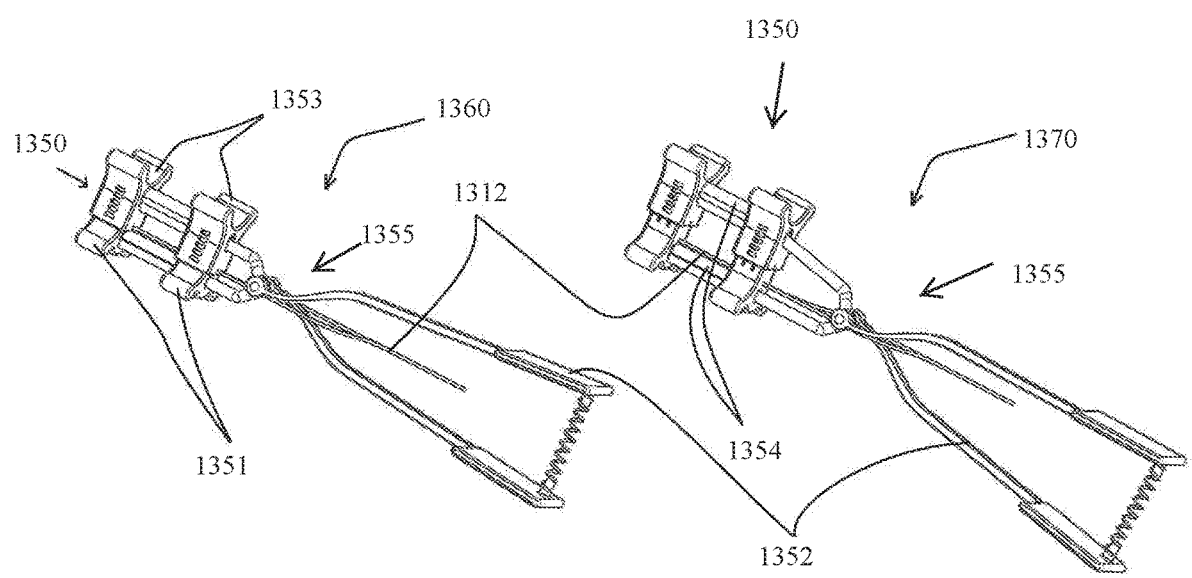
FIGS. 13F-13G are perspective views, collapsed and open, respectively, of an expanding dual bi-polar fecal incontinence device with an applicator, according to an exemplary embodiment of the invention.

FIGS. 13F-13G are perspective views, collapsed 1360 and open 1370, respectively, of an expanding dual bi-polar fecal incontinence device 1350 with an applicator, according to an exemplary embodiment of the invention. Device 1350 is composed of two or more sets of upper poles 1353 and lower poles 1351 (a "set" comprising an upper pole associated with a lower pole, similar to device 1300 shown in FIGS. 13A-13B) connected by connection bars 1354. Each lower pole 1351 has a locking mechanism 1308 with a separate removal string 1312. All removal strings 1312 are connected in their proximal ends to allow simultaneous transfer to the closed state 1360 by pulling the removal strings 1312.

FIGS. 13H-13J are cross-sectional views of the device 1350 and applicator 1355 showing the expansion mechanism of the applicator, according to an exemplary embodiment of the invention. In an embodiment of the invention, the applicator 1355 is constructed of two handles 1352, two arms 1358 an axis 1356 connecting the arms 1358 and the handles 1352 and a spring 1357. When the handles 1352 are pressed towards each other, the spring 1357 is compressed and the arms 1358 are rotated outwards and expand the device 1350 (FIG. 13I). When the press on the handles 1352 is released, the spring 1357 pushes the handles 1352 outwards back to their initial position (FIG. 13J).

FIG. 13K shows an expansion method using the applicator 1355 wherein controlled directional 1359 maneuvering of the handles 1352 expands the device 1350 gradually, according to an exemplary embodiment of the invention.

FIGS. 13L-13M show the locking mechanism between the handles 1352 and the arms 1358. A radial array of teeth 1362 on the arms 1358 matches another radial array of counterpart teeth 1364 on the handles 1352. When the handles 1352 are pressed, their rotation is transferred to the arms 1358 through contact of the counterpart teeth 1364 and the arms teeth 1362. When the handles 1352 are released, the counterpart teeth 1364 are leaping over the arms teeth 1352 as a result of the slanted back faces of the teeth. Thus the arms 1358 keep their rotated position when the handles 1352 are returning to their initial position.

Figure 13N:
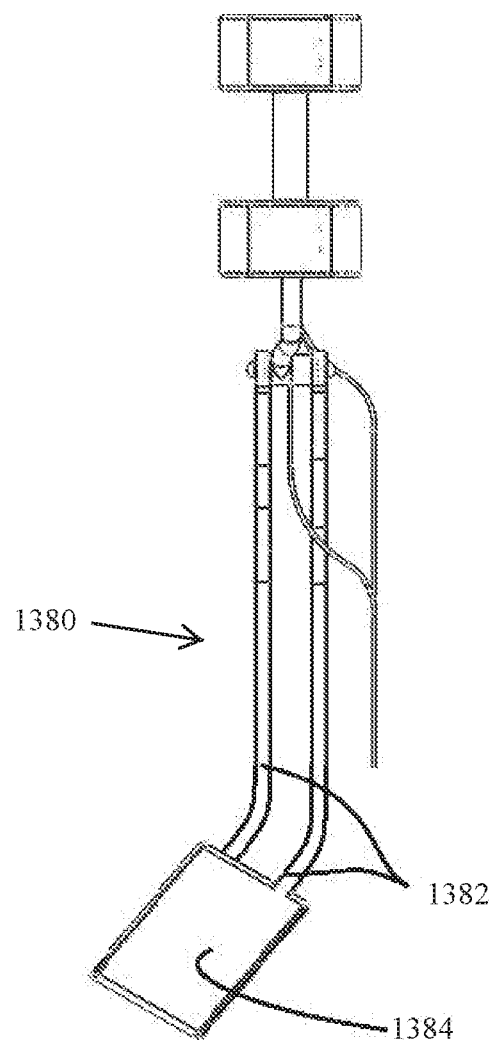
FIG. 13N is an isometric view of an applicator for use with the device of FIGS. 13F-13G with biased handles, according to an exemplary embodiment of the invention.

FIG. 13N is an isometric view of an applicator 1380 with biased handles for use with the device 1350, according to an exemplary embodiment of the invention. In an embodiment of the invention, the pressing surfaces 1384 of the handles 1382 are bent to one side to allow a more convenient user hold of the applicator 1380.

In some embodiments of the invention, devices 1300, 1350 are activated by means of a screw rod, whereby turning the screw rod opens or collapses the device 1300, 1350.

In some embodiments of the invention, the devices 1300, 1350 are activated by a piston.

Figure 14A:
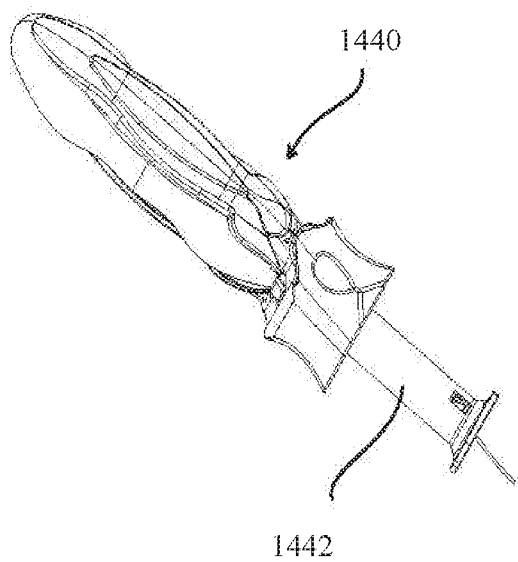
FIGS. 14A and 14B, taken together, are perspective views of a support ring part and a rectal pressing part, respectively, of a two-part fecal incontinence device with each part's applicator, according to an exemplary embodiment of the invention.
Figure 14B:
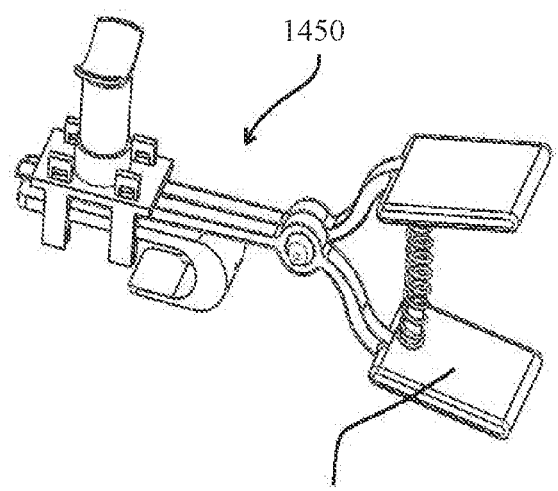

FIGS. 14A and 14B, taken together, are perspective views of a support ring part 1440 and a rectal pressing part 1450, respectively, of a two-part fecal incontinence device 1400 with each part's applicator 1442, 1452, according to an exemplary embodiment of the invention. In an embodiment of the invention the support ring part 1440 is supplied with a particular applicator 1442 for the insertion and deployment of the support ring part 1440. Once the support ring part 1440 is deployed in the vagina and its applicator 1442 is removed, the rectal pressing part 1450 is inserted using its particular applicator 1452 and reversibly attached to the support ring part 1440.

Figure 14C:
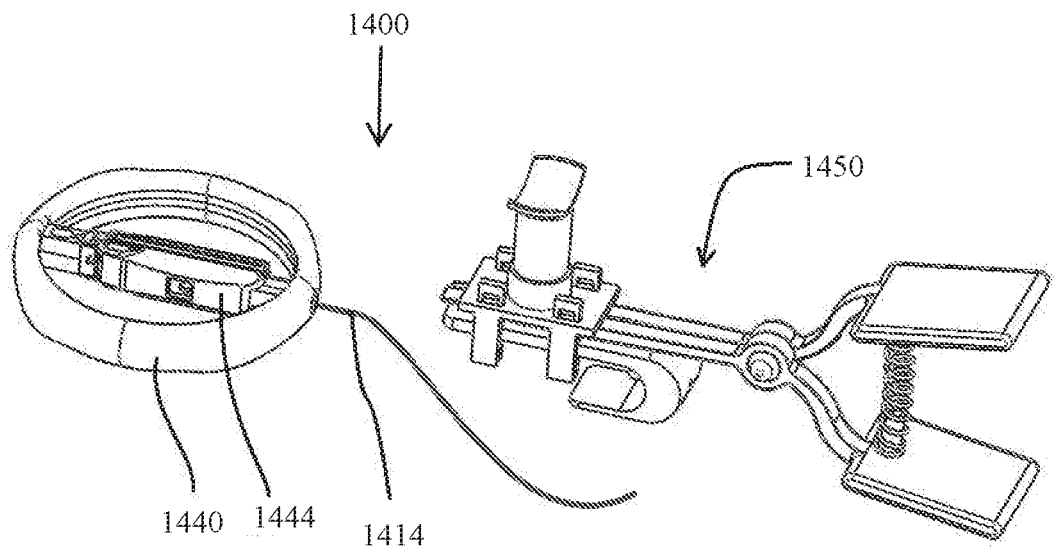
FIGS. 14C-14D are perspective views of the rectal pressing part being placed over the support ring part, according to an exemplary embodiment of the invention.
Figure 14D:
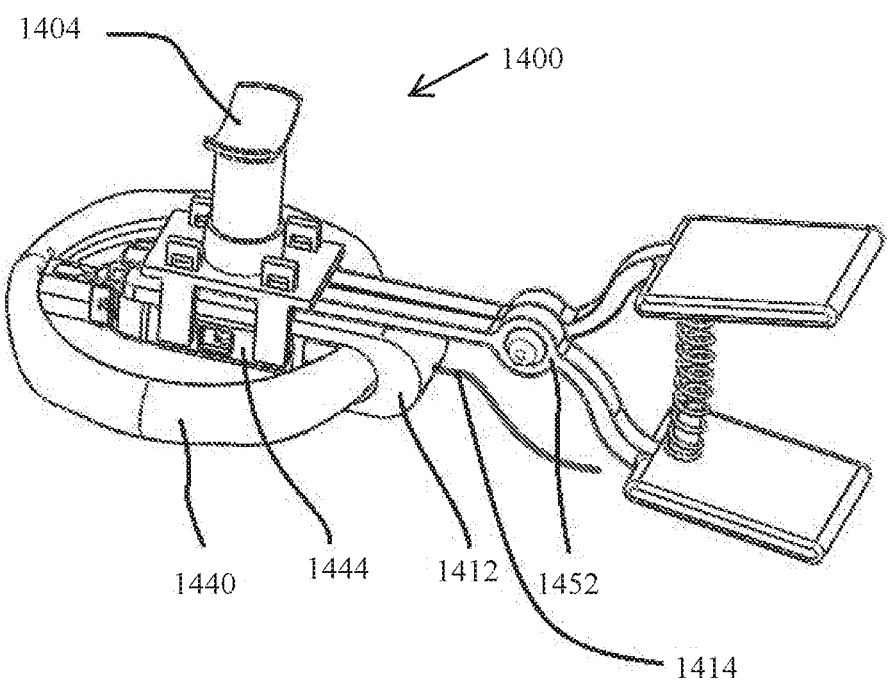

FIGS. 14C-14D are perspective views of the rectal pressing part 1450 being placed over the support ring part 1440, according to an exemplary embodiment of the invention. In an embodiment of the invention, the rectal pressing part 1450 is placed over the support ring part 1440 in a way that the rectal pressing part 1450 covers a central tube 1444 of the support ring part 1440. When assembled and/or expanded and/or deployed, at least the support ring part 1440 stabilizes the device 1400 in the patient's vagina and the rectal pressing part 1450 renders pressure to the rectum for providing fecal incontinence treatment.

FIGS. 14E-14F are perspective views, collapsed 1420 and open 1430, respectively, of the two-part fecal incontinence device 1400 with the rectal pressing part applicator 1452, according to an exemplary embodiment of the invention. In some embodiments of the invention, both the support ring part 1440 and the rectal pressing part 1450 assume their collapsed states during storage, insertion and removal. In some embodiments of the invention, the rectal pressing part 1450 is inserted and placed over the support ring part 1440 using its applicator 1452. The applicator 1452 serves also to expand a rectal pressing element 1404. By pressing the applicator handles 1454 towards each other, distal ends of the applicator 1452 arms are moved away from each other, thus pushing the rectal pressing element 1404 against the rectum, shown in FIG. 14F. The rectal pressing element 1404 has snaps 1406 that snap into slots 1408 in the rectal pressing mechanism base 1412 (FIG. 14H).

FIG. 14G is a perspective view of the device 1400 and FIG. 14H is a cross-sectional view of the device 1400, in accordance with an exemplary embodiment of the invention. In an embodiment of the invention, the rectum pressing element 1404 is shaped to anchor the device 1400 in regards to the rectum thus reduces the possibility of rotation while applying pressure on the rectum.

In an embodiment of the invention, there is a plurality of slots 1408 in the rectal pressing mechanism base 1412 providing the snaps 1406 with a plurality of locking positions to lock the rectum pressing element 1404 at different heights.

In an embodiment of the invention, when the applicator 1452 is removed, the proximal end of the removal string 1414 extends outside the vagina (similar to a conventional menstrual tampon). The removal string 1414 is connected to the snaps 1406. Pulling of the removal string 1414 causes the snaps 1406 to bend inward thus releasing the locking and allowing the device 1400 to return to its collapsed state 1420.

In some embodiments of the invention, the rectum pressing element 1404 is activated by means of a screw rod, whereby turning the screw rod opens or collapses the rectum pressing element 1404.

FIGS. 15A-15B are perspective views, collapsed 1520 and open 1530, respectively, of a piston activated fecal incontinence device 1500, according to an exemplary embodiment of the invention. In an embodiment of the invention, the device 1500 is made of a pessary 1502 and a rectum pressing system over the pessary. The device 1500 is inserted into the vagina using an applicator which is released and removed when the pessary is deployed (FIG. 15B).

In an embodiment of the invention, the rectum pressing element 1504 is activated vertically as part of a piston element. The rectum pressing element 1504 slides within a piston chamber 1506. A filling tube 1510 connects to the piston chamber 1506 at its bottom end. A unidirectional pressure valve 1512 allows air flow from a pump 1514 through the filling tube 1510 into the piston chamber 1506 and can be released to allow backflow. The rectum pressing element 1504 is held in its activated position by the pressurized air. When the unidirectional pressure valve 1512 is released, the pressure within the piston chamber 1506 is released and the rectum pressing element 1504 is deactivated and descends to its initial position.

In an embodiment of the invention, the pump 1514 may also be a reservoir for air or liquid or may be attached to such reservoir.

In an embodiment of the invention, when the device 1500 is deployed in the vagina a proximal end of a removal string 1518 extends outside the vagina (similar to a conventional menstrual tampon). The removal string 1518 is connected to the locking mechanism 1516. Pulling of the removal string 1518 causes the locking mechanism 1516 to bend inward thus releasing the locking and allowing the pessary 1502 to return to its collapsed state 1520.

In an embodiment of the invention pulling the removal string 1518 also releases the unidirectional pressure valve 1512, thus the rectum pressing element 1504 is deactivated simultaneously with the collapse of the pessary 1502.

Figures 16A, 16B:
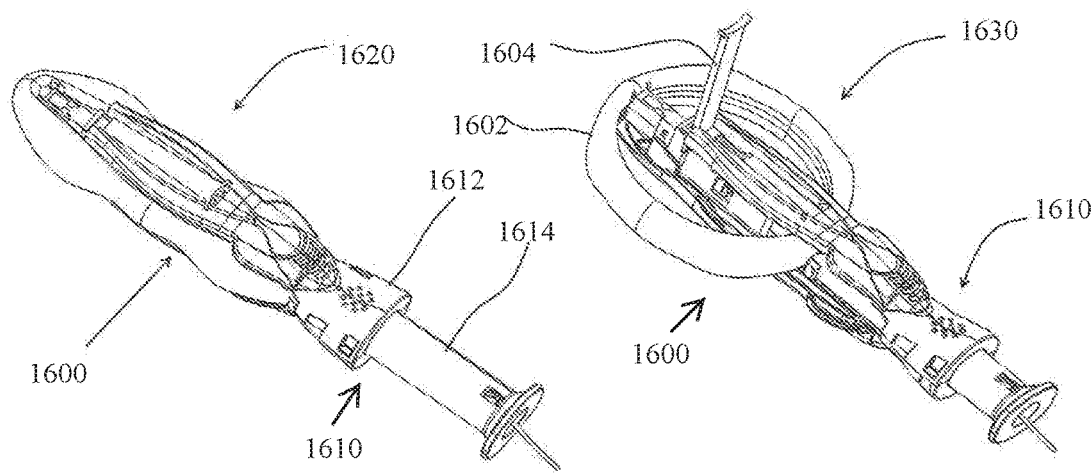
FIGS. 16A-16B are perspective views, collapsed and open, respectively, of a standing rectal pressing element fecal incontinence device with an applicator, according to an exemplary embodiment of the invention.

FIGS. 16A-16B are perspective views, collapsed 1620 and open 1630, respectively, of a standing rectal pressing element fecal incontinence device 1600 with an applicator 1610, according to an exemplary embodiment of the invention. In some embodiments of the invention, the device 1600 assumes the collapsed state 1620 during storage, insertion and/or removal. In some embodiments of the invention, the device 1600 assumes the expanded state 1630 after insertion.

In an embodiment of the invention, the device 1600 has an expandable pessary 1602 with a rectum pressing element 1604. In an embodiment of the invention, the rectum pressing element 1604 is activated angularly (in respect to the device 1600 mid plane). The rectum pressing element 1604 is shaped to anchor the device 1600 adjacent to the rectum, reducing the possibility of rotation, while applying pressure on the rectum.

In an embodiment of the invention, the applicator 1610 is attached to the device 1600 and used for insertion of the device 1600 into a vagina and/or for transforming the device 1600 from the collapsed state 1620 (FIG. 16A) into the expanded state 1630 (FIG. 16B). In an embodiment of the invention, the applicator 1610 comprises a holder 1612 and a pusher 1614. The holder 1612 and pusher 1614 are configured to allow axial movement of the pusher 1614 relative to the holder 1612, where the pusher 1614 moves axially within the holder 1612. Pushing the pusher 1614 causes the proximal end of the pessary 1602 to move towards the distal end of the pessary 1602, thereby shortening its overall length and causing an outward expansion.

Figure 16C:
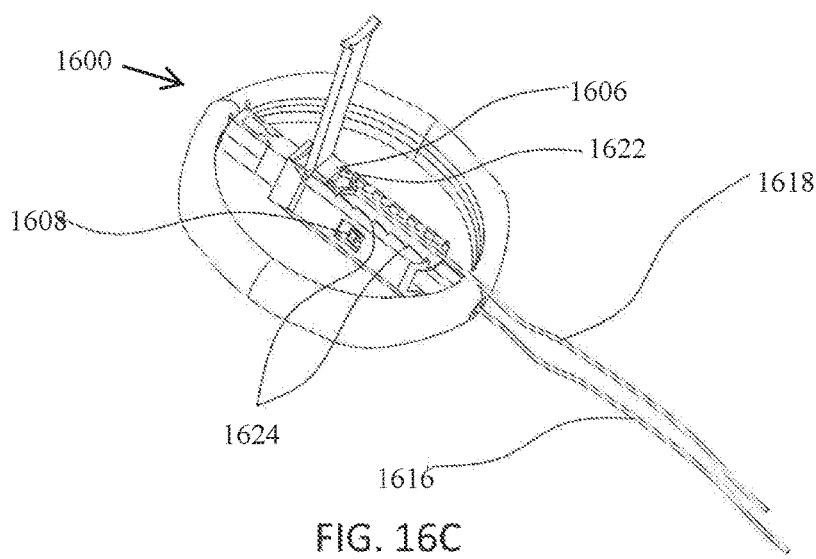
FIG. 16C is a perspective view of an open and deployed standing rectal pressing element fecal incontinence device, according to an exemplary embodiment of the invention.

FIG. 16C is a perspective view of an open and deployed standing rectal pressing element fecal incontinence device 1600, according to an exemplary embodiment of the invention. In an embodiment of the invention, the applicator 1610 activates the rectum pressing element 1604 by pushing the sliding locker 1606. Pushing the pusher 1614 in the distal direction causes the sliding locker 1606 to move axially causing the rectum pressing element 1604 to elevate. When the rectum pressing element 1604 is situated, the sliding locker 1606 prevents it from collapsing by two protruding arms 1622 that lock into corresponding groves 1624.

In some embodiments, the rectum pressing element 1604 is activated by an inflatable/deflatable balloon.

In an embodiment of the invention the sliding lock 1606 allows for device rectum pressing element's 1604 locking at different heights.

In an embodiment of the invention a locking mechanism 1608 prevents the pessary 1602 from transforming back from the expanded 1620 state to the collapsed state 1630.

In an embodiment of the invention, when the applicator 1610 is removed, a proximal end of the removal string 1616 extends outside the vagina (similar to a conventional menstrual tampon). The removal string 1616 is connected to the locking mechanism 1608. Pulling of the removal string 1616 causes the locking mechanism 1608 to bend inward thus releasing it and allowing the pessary 1602 to return to its collapsed state 1620.

In an embodiment of the invention, when the applicator 1610 is removed a proximal end of the FI removal string 1618 extends outside the vagina (similar to a conventional menstrual tampon). The FI removal string 1618 is connected to the sliding lock 1606. Pulling of the FI removal string 1618 causes the sliding lock 1606 to bend inward thus releasing it and allowing the rectum pressing element 1604 to return to its collapsed state.

In an embodiment of the invention both the removal string 1616 and the FI removal string 1618 are tied to each other at their proximal ends thus allowing simultaneous collapse of the rectum pressing element 1604 and the pessary 1602.

Figures 17A, 17B:
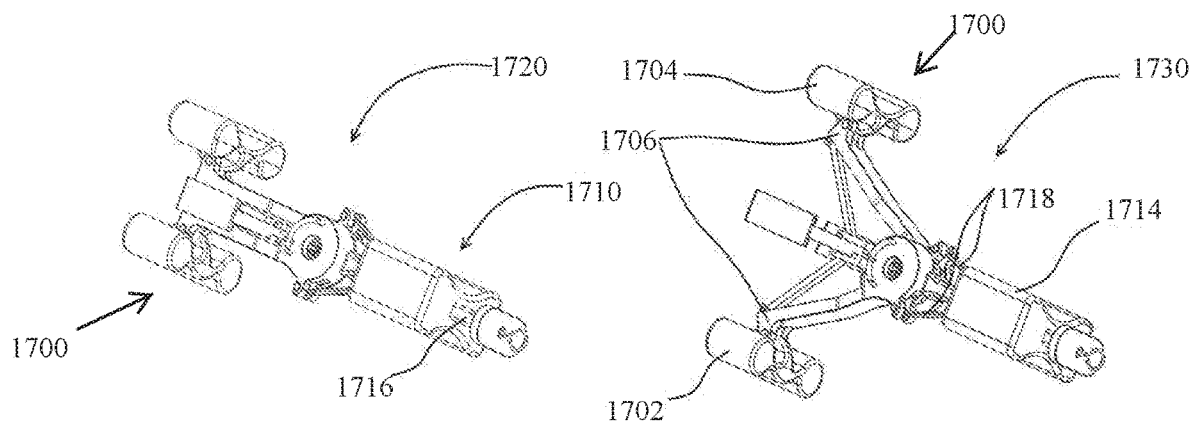
FIGS. 17A-17B are perspective views, collapsed and open, respectively, of a rotation activated fecal incontinence device with an applicator, according to an exemplary embodiment of the invention.

FIGS. 17A-17B are perspective views, collapsed 1720 and open 1730, respectively, of a rotation activated fecal incontinence device 1700 with an applicator 1710, according to an exemplary embodiment of the invention. In some embodiments of the invention, the device 1700 assumes the collapsed state 1720 during storage, insertion and/or removal. In some embodiments of the invention, the device 1700 assumes the expanded state 1730 after insertion.

Figure 17C:
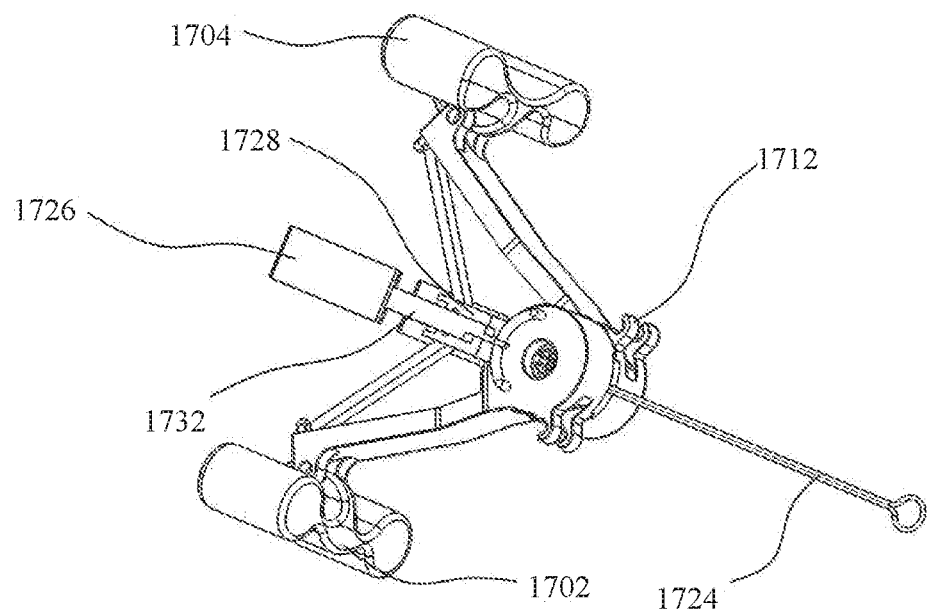
FIG. 17C is a perspective view of an open and deployed fecal incontinence device of FIGS. 17A-17B, according to an exemplary embodiment of the invention; and, FIG. 17D is a partial cross-sectional view of the fecal incontinence device of FIGS. 17A-17B showing a locking mechanism, according to an exemplary embodiment of the invention.

FIG. 17C is a perspective view of an open and deployed fecal incontinence device 1700, according to an exemplary embodiment of the invention. In an embodiment of the invention, the device 1700 is positioned on the sagittal plane applying pressure on the rectum and not obstructing the urethra. On the bottom of the device 1700 there is a rectum pressing element 1702 configured with a bulge to apply pressure to the rectum through the vaginal wall, which also provides resistance against and/or prevents the device 1700 from rotating. On the top of the device 1700 there anchoring element 1704 further anchoring the device and configured with a saddle to cup the urethra to prevent direct pressure on the urethra.

In an embodiment of the invention, the applicator 1710 is attached to the device 1700 through two arms 1718 protruding from the holder 1714 and connected to deployment hinges 1712. The two arms 1718 are used for insertion of the device 1700 into a vagina and/or for transforming the device 1700 from the collapsed state 1720 (FIG. 17A) into the expanded state 1730 (FIG. 17B).

In an embodiment of the invention, the applicator 1710 comprises a holder 1714 and a pusher 1716. The holder 1714 and pusher 1716 are configured to allow axial movement of the pusher 1716 relative to the holder 1714, where the pusher 1716 moves axially within the holder 1714. Pushing the pusher 1716 in the distal direction causes the device's arms 1706 to rotate opposite to each other, causing an outward expansion of the rectum pressing element 1702 and anchoring element 1704. This outward expansion applies pressure on the rectum and the vaginal wall. The two arms 1718 prevent the device 1700 from moving distally when pushed by the pusher 1716 and create a radial force on the device arms 1706 that rotates the device arms 1706.

In an embodiment of the invention there are side stabilizers 1726 that further prevent the device 1700 from rotating in the vagina. Expansion of the device arms 1706 causes an actuator 1728 to move distally. When the actuator 1728 moves distally it pushes outwards the side openers 1732 that expand the side stabilizers 1726 outwards. When expanded the side stabilizers 1726 press against the vaginal walls and prevent device rotation.

Figure 17D:
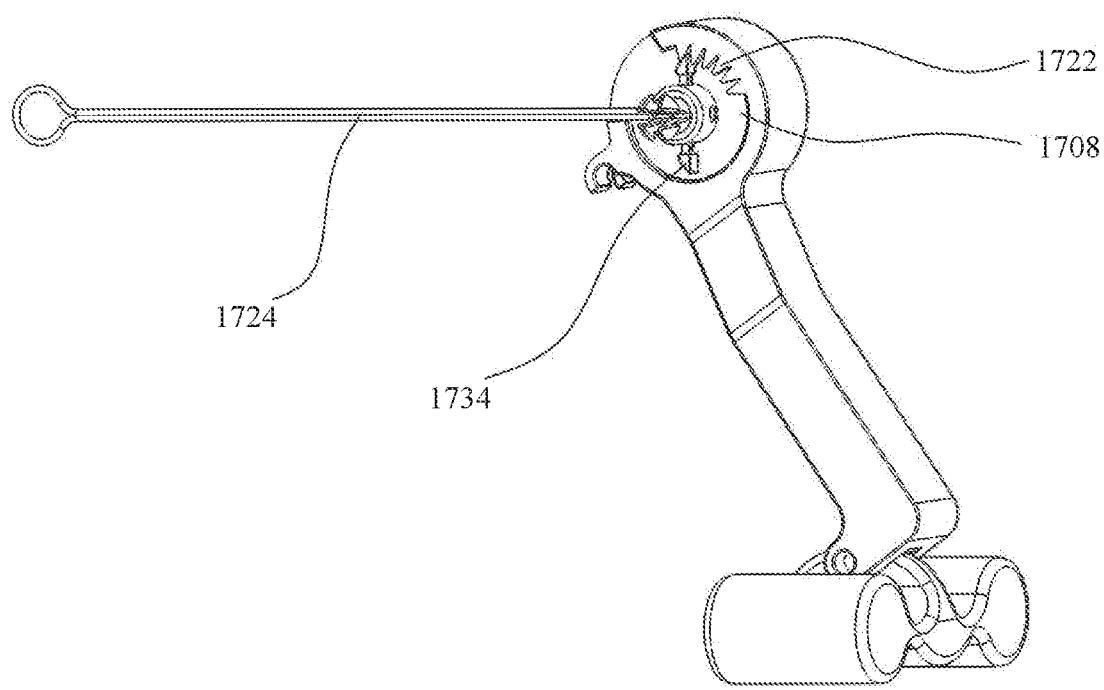

FIG. 17D is a partial cross-sectional view of the fecal incontinence device 1700 showing a locking mechanism 1708, according to an exemplary embodiment of the invention. In an embodiment of the invention, the locking mechanism 1708 prevents the device 1700 from transforming back from the expanded state 1730 to the collapsed state 1720 due to two locking teeth 1734 situated on an inner spring, that lock into opposite slots 1722.

In an embodiment of the invention the locking mechanism 1708 allows for device 1700 locking at different angles.

Once the device 1700 is in the expanded state 1730 proximal movement of the holder 1714 releases the holder's arms 1718 from the deployment hinges 1712. In an embodiment of the invention, when the applicator 1710 is removed a proximal end of the removal string 1724 extends outside the vagina (similar to a conventional menstrual tampon). The removal string 1724 is connected to the locking teeth 1734. Pulling of the removal string 1724 causes the locking teeth 1734 to move inward thus releasing them from the slots 1722 and allowing the device 1700 to return to its collapsed state 1720.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Further, described ranges are intended to include numbers outside any range described within statistical error and/or inherent measurement equipment limitations.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A fecal incontinence device for insertion into a vagina, comprising:
 a plurality of shell segments, which together form an enclosed cylinder with rounded ends in a collapsed state of the device, wherein one of the plurality of shell segments is disposed in the device facing a posterior wall of the vagina when the device is inserted into the vagina;
 a pressure generating structure attached to and abutting a posterior-facing the plurality of shell segments;
 a state-changing mechanism configured to reversibly transition the device from the collapsed state to an expanded state; and,
 an applicator, removable from the device, inserted into the enclosed cylinder and configured to activate the state-changing mechanism to transition the device from the collapsed state to the expanded state.

2. The device of claim 1, wherein the plurality of shell segments comprises two hemispherical shell segments, an upper shell segment and the posterior-facing shell segment, and the pressure generating structure is a bulge located on an exterior surface of the posterior-facing cylindrical shell segment.

3. The device of claim 1, wherein there are three or more shell segments, including the posterior-facing shell segment, and the pressure generating structure is a reversibly extendible pressure pole which is configured to be retracted within the posterior-facing shell segment when the device is in the collapsed state and extended when the device is in the expanded state.

4. The device of claim 3, wherein the pressure pole is at least one of extended and retracted by at least one of magnetic and mechanical force.

5. The device of claim 4, wherein a degree of extension of the pressure pole is controlled by at least one of magnetic field intensity and reversibly locking integral snaps located in the posterior-facing shell segment.

6. The device of claim 4, wherein the pressure pole is at least one of extended and retracted by a worm gear.

7. The device of claim 2, wherein the state-changing mechanism includes an actuator connected to a rack by a detachable holder and where the rack is operatively connected to at least one threaded pole by a plurality of cog wheels, wherein the actuator is configured to move coaxially in the holder, and wherein movement of the actuator in a distal direction causes movement of the shell segments towards the expanded state of the device and movement of the actuator in a proximal direction causes movement of the shell segments towards the collapsed state of the device.

8. The fecal incontinence device of claim 2, wherein one of the plurality of shell segments is configured with at least one fender configured to stabilize the fecal incontinence device in an anterior-posterior intra vaginal arrangement.

9. The device of claim 3, wherein the state-changing mechanism includes a puller and a holder, in contact with a central tube having a hinged connection with at least one arm for each of the shell segments.

10. The device of claim 9, wherein the puller has a plurality of pulling rods with bulges that are attached to a slider which also has hinged connection with each arm of the shell segments, wherein when the holder is pushed in a proximal direction, the pulling rods pull the slider over the central tube in a distal direction thus shortening the distance between the slider and the hinged connection, changing a state of the device from the collapsed state to the expanded state.

11. The device of claim 10, further comprising press blocks of an inner rotating mechanism on both sides of the puller wherein the press blocks push the bulges on the pulling rods which causes the pulling rods to rotate, aligning the pulling rods with an opening in the slider, and allowing detachment of the pulling rods from the slider.

12. A fecal incontinence device, comprising:
an outer shell cylindrically shaped and rounded on both ends;
a plurality of front support arms hingedly attached to the outer shell and configured to anchor the device;
a plurality of rear arms hingedly attached to the outer shell and configured to support the device, wherein at least one of the rear arms is further configured to apply rectal pressure; and,
a state-changing mechanism configured to transition the device from a collapsed state to an expanded state,
wherein the front support arms and the rear arms lie flush to an exterior surface of the outer shell when the device is in the collapsed state.

13. The device of claim 12, wherein the state-changing mechanism comprises a central activation shaft with tapered surfaces and where each of the front support arms and the rear arms has a free edge in contact with one of the tapered surfaces such that when the shaft is moved proximally the shaft forces the front support arms and the rear arms to rotate around hinges of the front support arms and the rear support arms and transition the device from the collapsed state to the expanded state.

14. The device of claim 13, wherein the tapered surfaces have a different angle for the rear arms than for the front support arms, resulting in a different range of motion for the rear arms with respect to the front support arms.

15. The device of claim 13, further comprising an applicator including a holder and a pusher, where the pusher moves axially within the holder.

16. The device of claim 15, wherein the pusher is in contact with the activation shaft such that pushing the pusher distally causes movement of the activation shaft distally, opening the front support arms and the rear arms outwards and into the expanded state.

17. The device of claim 15, wherein the holder has two sets of snaps situated on grooves at a front end of the device, such that the two sets of snaps prevent the device from moving distally during insertion of the device into the vagina.

18. The device of claim 17, wherein the applicator is configured to be rotatable around a longitudinal axis of the device, and wherein the two sets of snaps are configured to be bendable by rotation of the applicator, releasing them from slots and allowing for removal of the applicator.

19. The device of claim 13, further comprising a plurality of locking snaps on the activation shaft that snap into slots on the device and prevent the activation shaft from moving in a distal direction, keeping the front support arms and the rear arms opened and the device in the expanded state.

20. The device of claim 19, wherein the slots are configured in a plurality of locations on the device that allow locking of the activation shaft in several positions, thus creating multiple expansions options for the front support arms and the rear arms.

* * * * *